United States Patent [19]

Itó et al.

[11] 4,143,541
[45] Mar. 13, 1979

[54] METHOD AND DEVICE FOR MEASURING THE CHARACTERISTICS OF PLASTIC FLUID AND CONTROL SYSTEM FOR POURING THE SAME INTO MOULDS

[75] Inventors: Yasuro Itó, No. 4-38-16 Numabukuro, Nakano-ku, Tokyo, Japan; Hideharu Kaga, Tokyo, Japan; Yasuhiro Yamamoto, Kawasaki, Japan; Tadayuki Sumita, Tokyo, Japan; Kuniomi Suzuki, Tokyo, Japan; Kenji Kuroha, Tokyo, Japan; Takakazu Ishii, Tokyo, Japan; Mitsutaka Hayakawa, Kamakura, Japan

[73] Assignees: Yasuro Ito; Taisei Corporation, both of Tokyo, Japan

[21] Appl. No.: 763,664

[22] Filed: Jan. 28, 1977

[30] Foreign Application Priority Data

Jan. 27, 1976 [JP] Japan .................. 51-7132
Dec. 28, 1976 [JP] Japan .................. 51-157452

[51] Int. Cl.² ........................................ G01N 11/08
[52] U.S. Cl. ................................................. 73/55
[58] Field of Search ........................ 73/55, 56, 53, 54

[56] References Cited

U.S. PATENT DOCUMENTS

| 1,810,992 | 6/1931 | Von Dallwitz-Wegner | 73/55 |
| 3,520,179 | 7/1970 | Reed | 73/55 |
| 3,559,464 | 2/1971 | Foust et al. | 73/55 |
| 3,610,026 | 10/1971 | Topham | 73/55 |
| 3,839,901 | 10/1974 | Finkle et al. | 73/54 |
| 3,952,577 | 4/1976 | Hayes et al. | 73/55 |

FOREIGN PATENT DOCUMENTS

381640 8/1973 U.S.S.R. ............................ 73/54

Primary Examiner—Richard C. Queisser
Assistant Examiner—Joseph W. Roskos
Attorney, Agent, or Firm—Birch, Stewart, Kolasch and Birch

[57] ABSTRACT

The fluidity of a plastic fluid, cement mortar for example, is measured by passing the fluid through a flow passage packed with an aggregate for simulating an actual mould, measuring the flow pressure, and measuring the quantitative flow coefficient between the fluid and the flow passage. The pressure remaining in the passage after the fluid has been poured into the passage and after the flow speed has been decreased to zero or the pressure after a quantity of the fluid has been added to the passage and prior to the discharge of the fluid from the passage is measured to determine the relative shear stress yielding value. Thereafter, the fluid is caused to flow to determine again the relative shear stress yielding value, and the relative closure coefficient is determined by the difference between said two relative shear stress yielding values. After the elapse of a predetermined time the plastic fluid is caused to flow under a pressure and the pressure at the commencement of the flow is measured to quantitatively determine the variation in the shear stress yielding value with time, thereby determining the relative initial flow pressure. The relative flow viscosity coefficient is measured by varying the flow speed of the plastic fluid and by determining the relationship between the speed and the pressure of the plastic fluid. In the actual moulding operation the plastic fluid is prepared by using the factors thus determined and the pouring conditions are predetermined, or automatically controlled.

30 Claims, 26 Drawing Figures

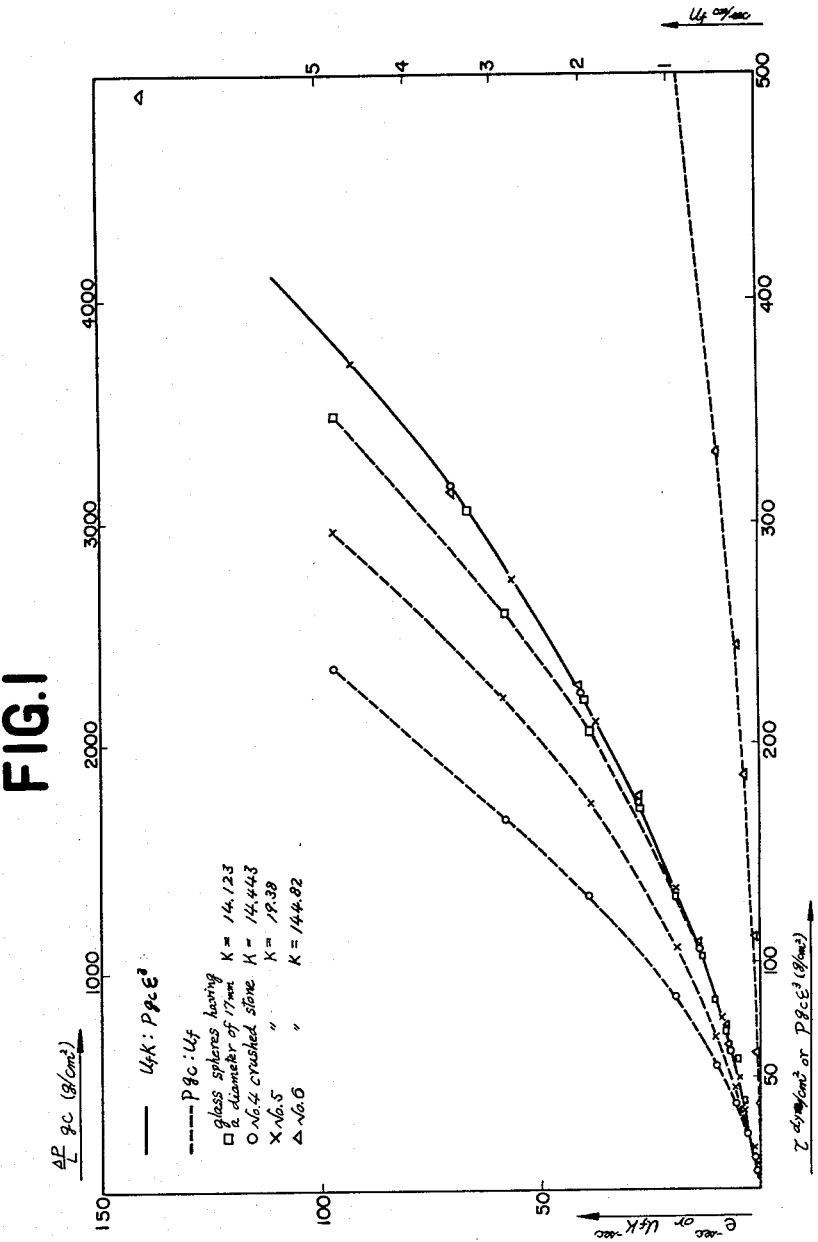

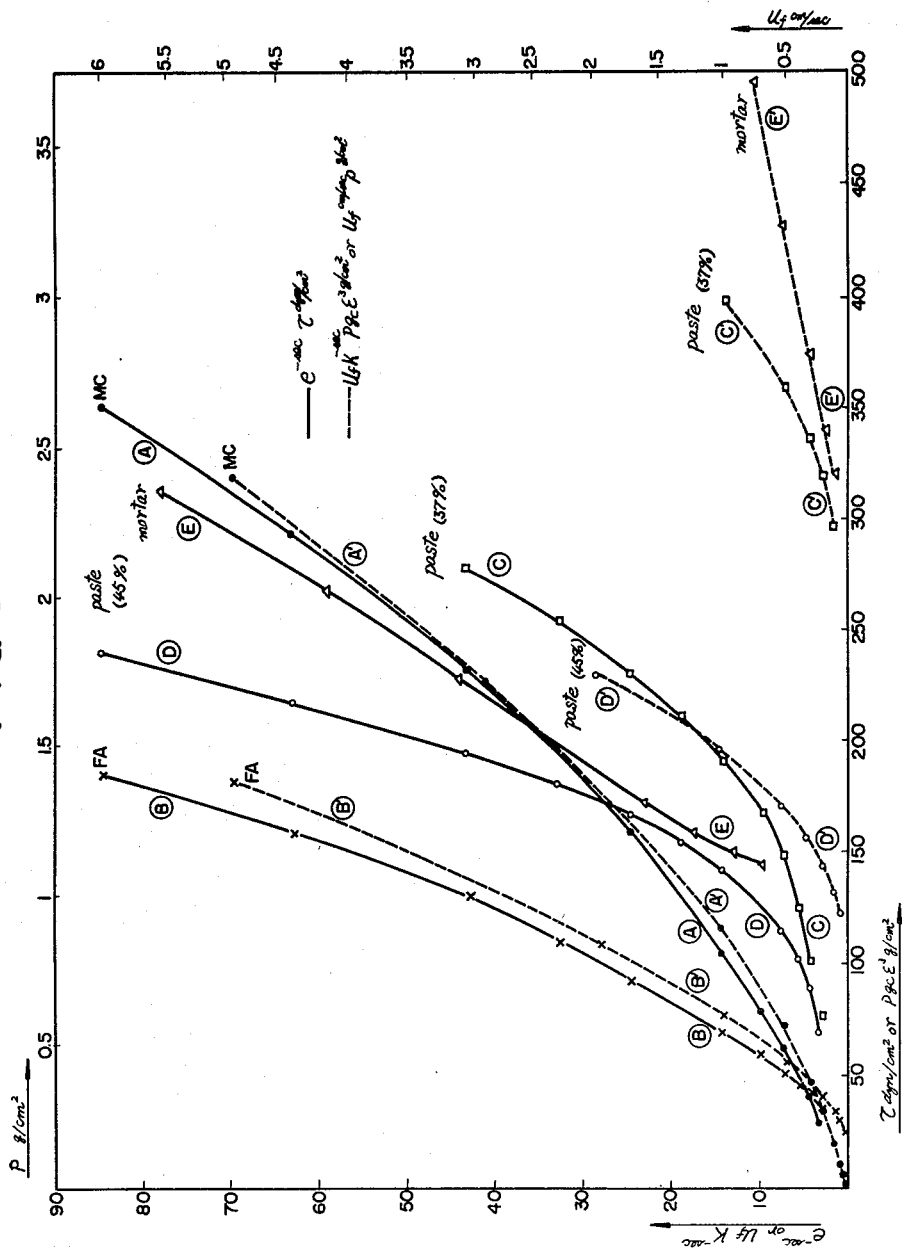

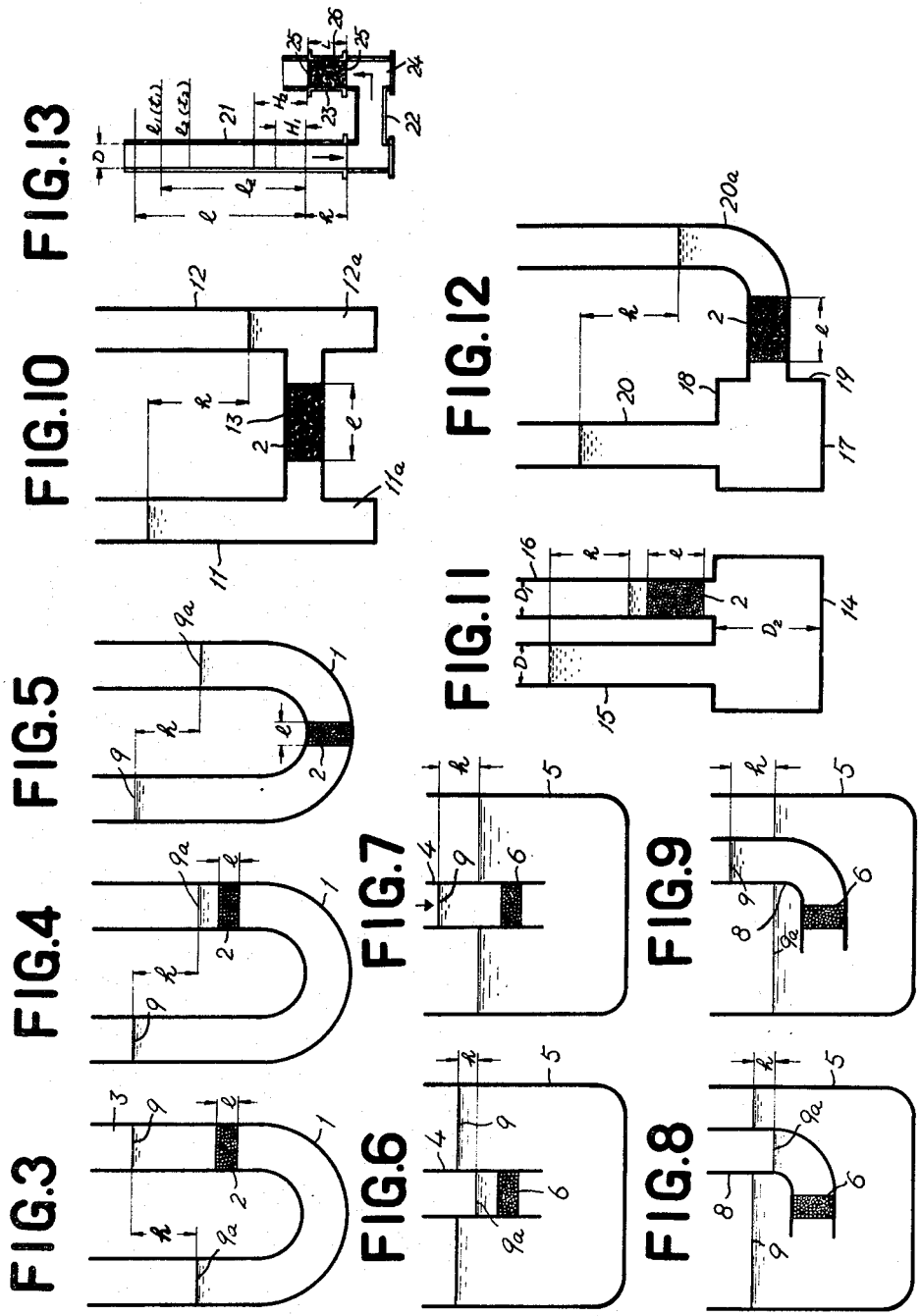

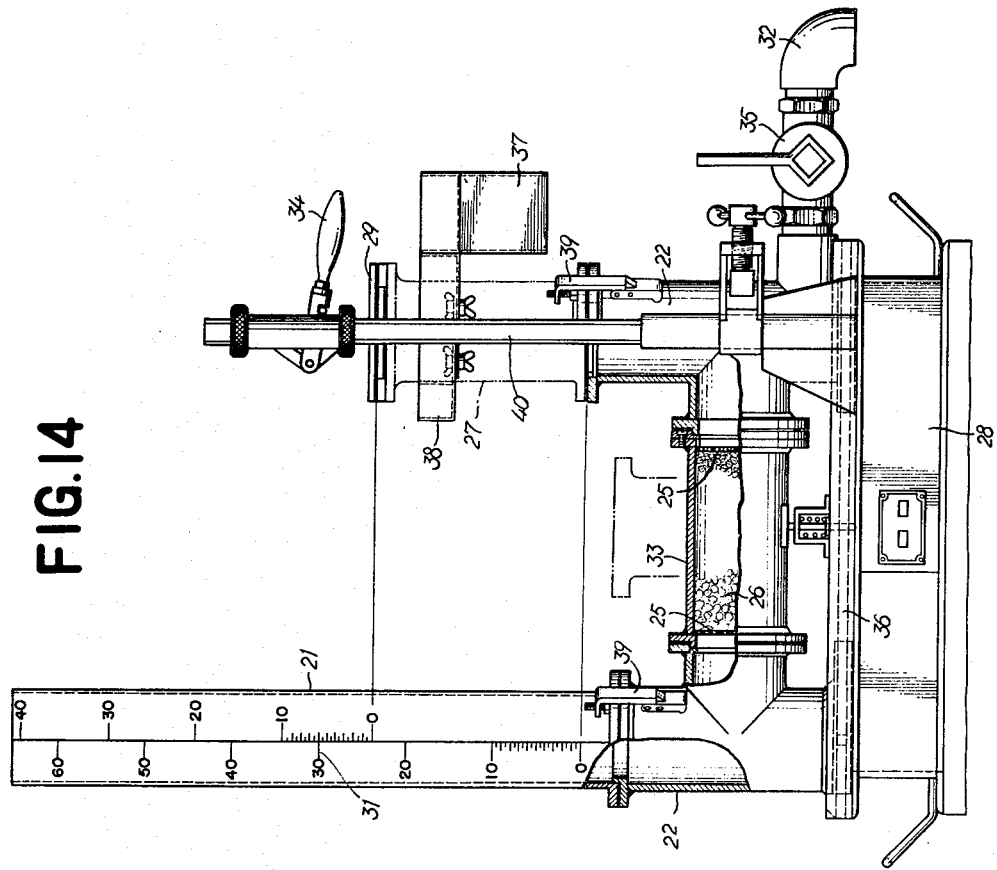

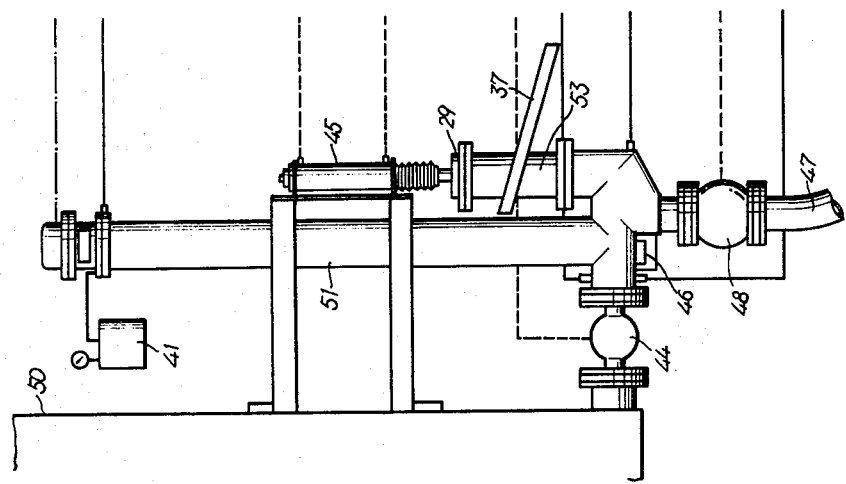
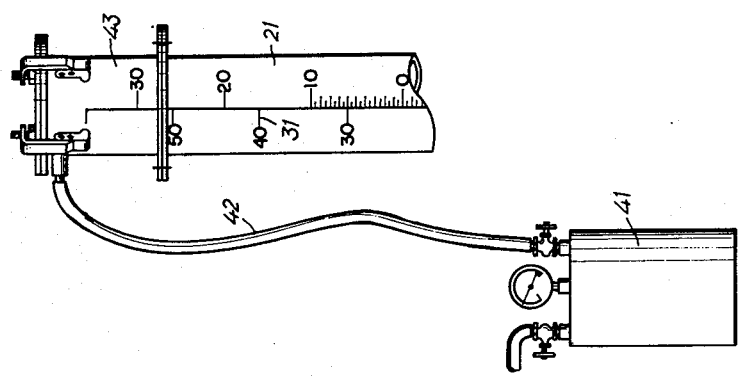

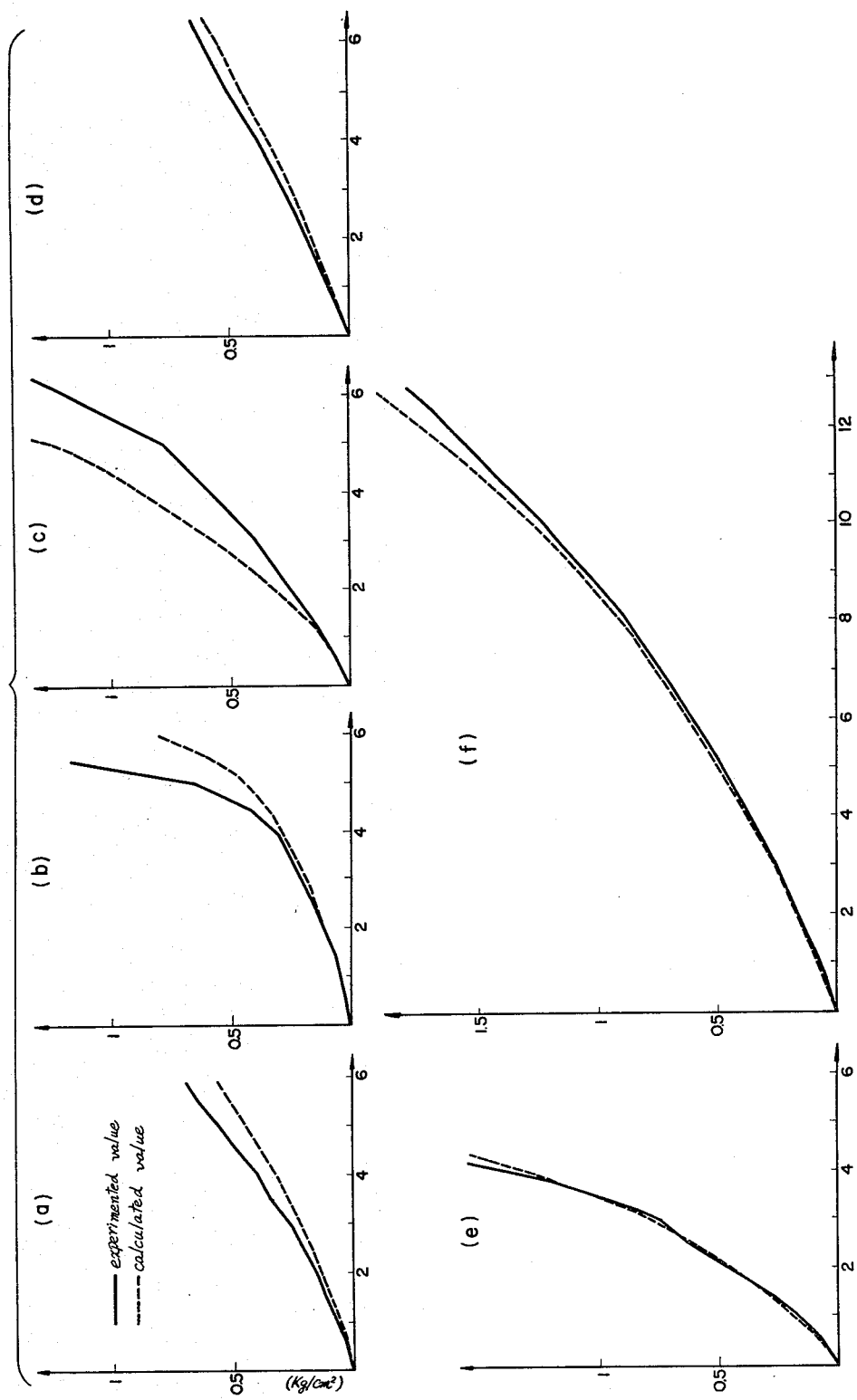

METHOD AND DEVICE FOR MEASURING THE CHARACTERISTICS OF PLASTIC FLUID AND CONTROL SYSTEM FOR POURING THE SAME INTO MOULDS

BACKGROUND OF THE INVENTION

The present invention relates to a method of measuring the fluidity of plastic fluids, a method of preparing the same, a method of pouring the same and apparatus for carrying out these methods.

When preparing or constructing residence houses, buildings, civil work structures, furnaces, metallurgical installations, and structural members such as walls, bricks and blocks by using cement, plaster, clay or other refractory substances, plastic fluids are poured or cast or packed into spaces, for example, narrow or crooked passages in which reinforcing iron bars or structural members are arranged or into interstices between aggregates which act as resistive elements to the flow of the plastic fluids. Various authorities, theories, and results of study regarding the fluidity of such plastic fluids have been reported or proposed. Yet accurate analysis has not yet been possible.

More particularly, according to the regulation of the Japanese Institute of Architecture (JASS, ST-701) and the Japanese Institute of Civil Engineering, a flow down testing device termed of P funnel, that is a funnel shaped measuring device having a discharge opening of a predetermined diameter at the bottom is used for determining the fluidity in accordance with the time (flow value) required for the plastic fluid, for example a cement composition, contained in the measuring devices to discharge through the discharge opening.

Of course, such flow value is a measure indicating the fluidity, but according to the result of our test regarding a prepacked mould in which the pouring pressure and other pouring conditions of a hydraulic setting composition such as cement are determined based on the flow value, it was found that it is difficult to establish a definite relationship between the flow value and the pouring conditions. Consequently, even in a composition having a relatively low flow value, it is difficult or impossible to pour it in some cases. In other words, by utilizing the result of measuring the fluidity by the P funnel it is impossible to satisfactorily practice the prepacked process to obtain products of high quality. In case when the pouring is difficult or impossible it is necessary not only to change the method of preparation of the plastic composition such as mortar but also to disassemble the casting mould for exchanging the coarse aggregate. Moreover, the strength and other characteristics of the products are not excellent.

According to the previous theory and research, the viscosity coefficient utilized to determine the fluidity was measured by a rotary viscosimeter. However, as a result of our extensive analysis we have found that the result of measurement of the fluidity of plastic fluids by this method is doubtful.

It has already been reported that cement mortar, paste or the like manifest the characteristics of Bingham fluid, but regarding the flow characteristic of the mortar comprising a complex suspension when it is poured into a mould packed with an aggregate having irregular size and shape no report has yet been made. The Bingham fluid is characterized in that it will flow only when a force larger than a predetermined value is applied to it, and the shear stress acting upon the plastic fluid when it begins to move is termed an initial shear stress yielding value or point. However, no efficient method or device for detecting the initial shear stress yielding value is known. In the past, this value was obtained from the flow speed determined by the P funnel or the viscosity determined by the rotary viscosimeter. In the pouring of a cement mortar into a mould (hereinafter, this term is used to mean not only ordinary moulds but also any spaces or voids of buildings or structures to be filled with cement mortar) the configuration of the voids or interstices in the aggregate such as gravel and crushed stone is extremely complicated so that the flow of the poured cement mortar through the voids is extremely complicated. For this reason, the actual performance of the cement mortar poured into a prepacked mould can never be simply anticipated by the prior art method described above, and it has been necessary to determine the initial shear stress yielding value by many experiments which is of course troublesome and expensive.

SUMMARY OF THE INVENTION

Accordingly, it is an object of the present invention to provide a novel method and measuring device capable of simulating the flow condition of the plastic fluid poured into a prepacked mould and providing such valuable factors as the fluidity, flow pressure, quantitative relative flow coefficient, relative shear stress yielding value, relative closure constant, and relative flow viscosity coefficient, etc., which are used to determine optimum pouring conditions.

Another object of this invention is to provide a control system for pouring a plastic fluid into a mould prepacked with an aggregate under optimum pouring conditions.

According to one aspect of the present invention there is provided a method of measuring the fluidity of a plastic fluid comprising the steps of passing the plastic fluid through a flow passage containing a resistance element manifesting a resistance to the flow of the plastic fluid, measuring the flow pressure, and determining a quantitative relative flow coefficient between the plastic fluid and the flow passage.

According to another aspect of this invention there is provided a method of measuring the fluidity of a plastic fluid comprising the steps of passing the plastic fluid through a flow passage containing a resistive element manifesting a resistance to the flow of the plastic fluid, measuring the pressure remaining in the flow passage after the plastic fluid has been poured into the flow passage and the flow speed has reduced to zero or the pressure after an additional quantity of the plastic fluid has been added to the flow passage and prior to the discharge of the plastic fluid from the flow passage, and quantitatively determining the relative shear stress yielding value between the flow passage and the plastic fluid.

By repeating the measurement of the relative shear stress yielding value and by calculating the difference between the relative shear stress yielding values successively measured, a relative closure coefficient between the plastic fluid and the flow passage can be determined. Further, after determining the relative closure coefficient, the pressure of the plastic fluid when it begins to flow through the flow passage after elapse of a predetermined time is measured and this process step is repeated to quantitatively determine the variation with time of the shear stress yielding value as well as the quantitative relative initial flow pressure of the plastic fluid relative to the flow passage.

According to another aspect of the present invention there is provided a method of measuring the fluidity of a plastic fluid comprising the steps of filling the plastic fluid in a flow passage containing a resistive element manifesting a resistance to the flow of the plastic fluid, causing the plastic fluid to flow through the flow passage under varying flow speed, measuring the relationship between the speed and pressure of the flow of the plastic fluid and determining the relative flow viscosity coefficient between the plastic fluid and the flow passage.

According to still another aspect of the present invention there is provided a method of measuring the pouring characteristic of a plastic fluid containing a solid component comprising the steps of preparing a U shaped tube, packing an aggregate in the tube for a predetermined length, pouring the plastic fluid into the tube through one end thereof with the other end closed, opening the other end thereby permitting the plastic fluid to flow through the aggregate, measuring the flow quantity and flow time of the plastic fluid thereby determining the flow rate, and measuring the static head difference between the plastic fluid levels on both sides of the packed aggregate, and determining the shear stress yielding value of the plastic fluid from the static head difference.

According to further aspect of the present invention, there is provided a method of pouring a plastic fluid into a mould comprising the steps of passing the plastic fluid through a flow passage simulating the condition of the mould and containing a resistive element which resists to the flow of the plastic fluid, measuring the flow pressure, measuring a quantitative relative flow coefficient between the plastic fluid and the flow passage, planning a pouring program in accordance with the flow pressure, the quantitative relative flow condition and a predetermined pouring condition of the mould, and controlling the pouring speed and pressure of the plastic fluid poured into the mould.

According to still further aspect of this invention there is provided a measuring device for measuring the fluidity of a plastic fluid, especially a cement mortar or paste, comprising a tube having a pouring port at one end and a discharge port at the other end, a resistance element packed in the tube at an intermediate portion thereof for a predetermined length for affording a resistance to the flow of the plastic fluid, and means for causing the plastic fluid to flow through the resistance element.

Advantageously, the tube takes the form of a U having a horizontal or curved leg interconnecting the vertical legs of the U. The resistance element is used to simulate an aggregate packed in a mould and packed in one of the vertical legs or the curved or horizontal leg. The plastic fluid is caused to flow through the tube under atmospheric pressure or compressed air.

According to a still further aspect of the present invention there is provided a control system for pouring a plastic fluid into a mould packed with an aggregate, comprising a pump for pouring the plastic fluid into the mould, means for detecting the pressure of the plastic fluid poured into the mould, means for detecting the speed of the pump, a first comparator for comparing the detected speed with a predetermined reference speed, means for setting a predetermined pressure condition of the plastic fluid, means for setting the physical characteristic of the plastic fluid, a computer for calculating an optimum pouring pressure of the plastic fluid in accordance with the output from the first comparator, the predetermined pressure condition, and the physical characteristics, a second comparator for comparing the output from the computer and the output of the pressure detecting means, first display means for displaying the output from the first comparator, and a second display means for displaying the output from the second comparator.

BRIEF DESCRIPTION OF THE DRAWINGS

Other features and advantages of the invention can be more fully understood from the following detailed description taken in conjunction with the accompanying drawings in which:

FIG. 1 is a graph showing the result of measurement of the fluidity of various nonNewton fluids under different aggregate packing conditions;

FIG. 2 is a graph showing the fluidity of various plastic fluids measured by a rotary viscosimeter as well as the fluidity measured under an aggregate packed condition;

FIG. 3 is a diagrammatic representation of one example of the measuring device embodying the invention and its method of operation;

FIGS. 4 through 12 show modified measuring device in which FIGS. 4 and 5 show modifications utilizing pipes similar to that shown in FIG. 3; FIGS. 6 and 7 utilize a linear tube and a tank; FIGS. 8 and 9 utilize a L shaped tube; and FIGS. 10, 11 and 12 utilize tubes of special configurations designed to avoid influence of the flow resistance at the bent portion of the tube and the deposition of solid particles at the bottom upon the result of measurement;

FIG. 13 is a diagrammatic representation of another embodiment of the measuring device of this invention;

FIG. 14 is a side view, partially in section, showing the actual construction of the modification shown in FIG. 3;

FIG. 15 is a front view showing the embodiment shown in FIG. 14;

FIG. 16 is a front view showing a modification of the embodiment shown in FIG. 15, in which air pressure is also used to move the plastic fluid;

FIG. 17 is a front view of still another modification of the measuring device of the present invention attached to a concrete mixer;

FIGS. 18a through 18f are graphs showing the relationship between the calculated values and the experimental values;

DESCRIPTION OF THE PREFERRED EMBODIMENTS

Figure 19:
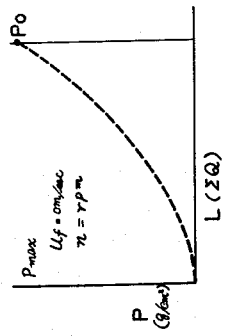
FIG. 19 is a graph showing the relationship between the pouring speed and pressure.

Before describing in detail the invention a theoretical analysis will be made at first.

In most cases, the following equation has been used for calculating the specific surface area Sm of irregular particles based on the Stokes' theorem for determining the fluidity of a Newton fluid flowing through the interstices of irregular particles.

$$Sm = \left\{ \frac{\Delta P g_c}{3\mu_N \xi U_f L_b \rho_p^2} - \frac{\epsilon^3}{(1-\epsilon)^2} \right\}^{\frac{1}{2}}$$

in which
 $\Delta P(g/cm^2)$: pressure difference,
 $g_c$ (g.cm/g.sec$^2$): unit conversion coefficient,
 $L_b = L(cm)$: pouring distance
 $U_f$(cm/sec): empty column speed
 $\epsilon$: void percentage of the irregular particles packed
 $\xi$: packing coefficient of the irregular particles,
 $\rho_p$ (g/cm$^2$): specific gravity of the packed particles The following equation A-2 is obtained when one determines the Newton fluid viscosity $\mu_N$ (g/cm.sec) from the above described equation $$\mu_N = \frac{\Delta P g_c}{L_b U_f} \frac{\epsilon^3}{3 Sm^2 \xi \rho_p^2 (1-\epsilon)^2} \quad \text{A-2}$$

The units of this equations are shown by $$g/cm \cdot sec = \frac{g/cm^2 \times g \cdot cm/g \cdot sec^2}{1/sec}$$

and the unit construction of this equation is the same as that of the following equation A-3 representing the viscosity of Newton fluids.

$$\mu_N = \frac{\tau yz \, (g/cm^2) \, gc \, (g \cdot cm/g \cdot sec^2)}{eyz \, (1/sec)} = (g/cm \cdot sec) \quad \text{A-3}$$

where
 $\tau yz$ (g/cm$^2$): shear stress
 $eyz$ (1/sec): shearing speed.

Denoting the term of the actual irregular particle by K(1/cm$^2$) in equation A-2, the following equation B-2 can be derived.

$$K(1/cm^2) = 3 Sm^2 \xi \rho_p^2 (1-\epsilon)^2 \quad \text{B-2}$$

Expressing the viscosity $\mu_N$ of the Newton fluid by a common viscosity $\eta$ and denoting $\Delta p$ as a pressure Pg/cm$^2$ the equation A-2 can be written as follows $$\eta = \frac{P \cdot g_c \cdot \epsilon^3}{1 - U_f \cdot K} = \frac{P \cdot g_c \cdot \epsilon^3}{U_f K} \, (g/cm \cdot sec) \quad \text{B-3}$$

Thus, the shear stress term $\tau yz$ corresponds to $P \cdot g_c \, \epsilon^3$ and the shearing speed term $eyz$ to $U_f/K$.

Referring now to FIG. 1 dotted line curves show the relationship between the speed and pressure and solid line curves show the fluidity measured by a rotary viscosimeter when 1% aqueous solution of methylcellulose which is a non-Newton fluid is passed through glass spheres having a diameter of 17 mm and through Nos. 4, 5 and 6 crushed stones, respectively. It was confirmed that respective measuring points determined by equation B-3 substantially coincide with the flow curves determined by the rotary viscosimeter so that $eyz = U_f/K$. From these results, the value of K can be calculated when the value of the specific surface area Sm is known. Conversely, the specific surface area Sm can be determined by using such non-Newton fluid as methylcellulose.

In our research the following five types of the fluid were prepared.
 A. 1% aqueous solution of methylcellulose
 B. 50% aqueous solution of flyash
 C. 37% aqueous solution of cement (cement paste)
 D. 45% aqueous solution of cement (cement paste)
 E. cement mortar in which the ratio of cement to sand (c/s ratio) is 1:1 and the ratio of water to cement (W/C ratio) is 47%.

Compositions A and B are non-Newton fluids, C, D and E are Bingham or non-Bingham fluids. These fluids were poured at different speeds into a cylinder having a diameter of 10 cm and a length of 50 cm in which is packed at a uniform density crushed stone having a size of 15-25 mm. The pouring speed and pressure were measured and the viscosity was measured by a rotary viscosimeter.

The results are shown in the graph shown in FIG. 2 in which the left ordinate represents the shearing speed e or $U_f/K$, the lower abscissa the shear stress $\tau$ and $Pg_c \epsilon^3$, the right ordinate the pouring speed $U_f$ and the upper abscissa the pressure P(g/cm$^2$). Each curve shows a direct proportionality, all data correspond each other, and equations B-1 and A-3 correspond each other. The solid lines show the values measured by the rotary viscosimeter while dotted lines the flow between the irregular particles. With reference to the 1% aqueous solution of methylcellulose curve Ⓐ — Ⓐ showing the viscosity obtained by the rotary viscosimeter substantially coincides with dotted curve Ⓐ' — Ⓐ' showing the flow between the irregular particles, so that it was found that it is possible to quantitatively adopt the viscosity obtained by the rotary viscosimeter. In the cases of the compositions C, D and E described above their flow curves Ⓒ — Ⓒ, Ⓓ — Ⓓ and Ⓔ — Ⓔ shown by solid lines and Ⓒ' — Ⓒ', Ⓓ' — Ⓓ' and Ⓔ' — Ⓔ' shown by dotted lines differ greatly showing quite different configuration, so that it is impossible to presume or expect the configuration of the dotted line curves by that of the solid line curves. Curves Ⓑ — Ⓑ and Ⓑ' — Ⓑ' are spaced only a little, but their configuration is similar to that of the composition A. This is caused by the characteristic of the flyash and may be attributed to the fact that the configuration of the particles is substantially spherical and that the ratio of water to flyash is large.

Thus, the result of our research revealed that, in the case of high concentration plastic fluids wherein the ratio of water to solid powder, such as cement, clay, plaster, etc., utilized for constructing buildings or civil structures is small, it is impossible to obtain a reliable quantitative value from equation A-1 by the prior art method of measuring the viscosity of plastic fluid by means of a rotary viscosimeter for the purpose of analyzing the flow characteristic of such high concentration plastic fluid.

The reason that the well known theory or the measurement of the prior art method is not reliable may be attributed to the Σ effect (a phenomenon in which particles of the composition gather at the center of the passage, or the low viscosity composition gathers at the periphery of the passage), lamination or the tendency of narrowing the passage which occurs when the plastic fluid flows through the interstices between the irregular particles. The prior art theory or method did not give any attention to these phenomena. In the cases of manufacturing concrete products, concrete structures or refractory structures, in order to reasonably arrange the coarse aggregate such as gravel or coarse refractory particles in the mould, to increase the mechanical strength and heat resistance property of the products and to economically use the cement, the so-called prepacked process is advantageous wherein the aggregate particles are prepacked in the mould and then the flowable plastic fluid is poured into the mould. According to this prepacked process, however, intricated interstices having a large resistance to flow are formed between the prepacked aggregate particles so that when mortar or concrete paste having complicated flow characteristics described above is poured in the prepacked mould, phenomena that can not be expected by the result of measurement obtained by the rotary viscosimeter frequently occur.

According to the present invention the fluidity of the plastic fluid of the type described above is determined relatively between the factors concerning the flow passage and the fluid thereby determining quantitative data that can be used as the practical index which are different from the qualitative tendency of the fluid. More particularly, the plastic fluids of this type such as a cement paste or concrete mortar or plaster mortar do not immediately flow when subjected to pressure but they are the so-called Bingham fluids which begin to flow when the pressure exceeds a particular value specific to each fluid. Regarding the Bingham fluid it is important to determine the pressure condition at which the fluid begins to flow, such pressure being termed an initial shear stress yielding value. The performance of the flow after commencement varies greatly which is called the flow viscosity coefficient. Where the plastic fluid of the type described above is passed through the flow passage described above, the flow quantity varies with time due to the closure of the passage thus varying the flow characteristics. This is called the closure coefficient. According to the present invention, the initial shear stress yielding value, the flow viscosity coefficient and the closure coefficient are not merely determined qualitatively but instead determined as relative quantitative quantities between the plastic fluid and the condition of the flow passage through which the plastic fluid flows. Thus, the invention is characterized in that the fluidity of the plastic fluid is determined by the three elements of the relative initial shear stress, the relative flow viscosity coefficient and the relative closure coefficient.

Regarding the initial shear stress yielding value and the initial flow viscosity coefficient, the resistance term they have been processed in the prior art as the viscosity, viscous property or the initial shear strength yielding value which merely represent the qualitative characteristics of the plastic fluid itself by fixing the resistance factor unvariably. The invention is characterized in that the fluidity is determined in accordance with the relative initial shear stress yielding value and the relative flow viscosity coefficient. The term relative closure coefficient is firstly used by us to mean the tendency of narrowing the passage due to the size of the particles, the size of the passage, and the deposition of the particles due to the difference in the specific gravity. We have confirmed that this coefficient is greatly influenced by the velocity and pressure of the fluid.

Certain examples of the measuring device of the present invention are illustrated in FIGS. 3 to 12. In the embodiments shown in FIGS. 3 to 5 the necessary static head difference is created by the measuring devices themselves, whereas in the embodiments shown in FIGS. 6 to 9, the static head difference is produced by using a tank containing cement mortar or the like. In the embodiments shown in FIGS. 10, 11 and 12, a plurality of component elements are used for making easy to handle the measuring device and to increase the accuracy of the measurement. In the embodiments shown in FIGS. 3, 4 and 5 a U shaped tube 1 is used and in the cases shown in FIGS. 3 and 4 a reference aggregate 2 or other aggregate is packed in one leg for a definite length l, and the fluidity of a plastic fluid is measured by passing the same through the aggregate. In the embodiment shown in FIG. 3, a pouring port 3 is provided for the leg containing the aggregate 2, whereas in the case shown in FIG. 4, the pouring port 3 is provided for the opposite leg. In each case, the upper end of the other leg is utilized as the discharge port. In the case shown in FIG. 5, the aggregate 2 is packed at the center of the bottom for the definite length l. To ensure the definite length it is advantageous to use metal wire nets on the opposite sides of the aggregate. For the same length l, the value of the static head difference h varies somewhat dependent upon in which leg is the aggregate is packed and the distance between the pouring port and the aggregate 2. For this reason, it is necessary to specify the leg acting as the pouring port during measurement for each measuring group. On the contrary, in the embodiment shown in FIG. 5, since the aggregate is packed at the middle point of the U shaped leg the result of measurement is the same irrespective which one of the legs is used as the pouring port, thus eliminating eroneous use. In the embodiments shown in FIGS. 3 and 4 since the aggregate 2 is located at the linear portion of the leg it is easy to clean, exchange the aggregate on which the plastic fluid has been deposited and solidified.

In the embodiments shown in FIGS. 6 and 7, a linear tube 4 is used and tank 5 containing mortar or the like is used as auxiliary means. In each case, the aggregate 6 is packed in an intermediate or bottom portion of the tube. In the embodiment shown in FIG. 6, the measurement is done by merely inserting the tube 4 into the plastic fluid contained in the tank, whereas in the embodiment shown in FIG. 7, the measurement is done by pouring the liquid into the tube 4 from above. In the embodiments shown in FIGS. 3 to 5, the measuring device is independent of the tank and can be used in any place without using any auxiliary device. In the embodiments shown in FIGS. 6 and 7, since in nearly all cases, the plastic fluid to be measured such as cement mortar is contained in a tank, the measurement can readily be performed by merely inserting a tube into the mortar. In each case, the static head difference h between the levels 9 and 9a at the pouring port and the discharge port respectively is determined a short time after pouring or insertion when the levels become calm. The embodiment shown in FIG. 6 is more convenient to use than that shown in FIG. 5 because it is only necessary to insert the tube but it is difficult to measure the position of the fluid level 9a formed in the inserted tube. In the embodiment shown in FIG. 7, it is somewhat troublesome to pour the fluid into the tube, the selection of the embodiments being determined according to the actual measuring condition. It is advantageous to provide a supporting leg for the linear tube 4 for the purpose of maintaining its height in the tank.

It can be readily noted that in the embodiments shown in FIGS. 3 to 7 the plastic fluid passages through the aggregate in the vertical direction which condition commensulating with the practical pouring or moulding conditions of the mortar in which the mortar is poured upwardly or downwardly. Of course, it is possible to use the result thus obtained for the case in which the plastic fluid is poured in the horizontal direction. Thus there is no basic difference whether the plastic fluid passes through the aggregate packed layer in the horizontal or vertical direction. Where it is necessary to use, without any correction, the measured value for the horizontally poured plastic fluid, measuring devices utilizing a L shaped tube 8 as shown in FIGS. 8 and 9 are preferred. In the case shown in FIG. 8, the tube 8 is immersed in the plastic fluid contained in the tank 5 whereas in the case shown in FIG. 9 the plastic fluid is poured into the tube from above. In each of the embodiment shown in FIGS. 3 to 9 a tube having a uniform inner diameter is used but it should be understood that the inner diameter of the tube may be varied. It is important, however, that the variation in the inner diameter will not affect the result of pouring the plastic fluid through the packed aggregate because the object of the measurement is to accurately determine the property of pouring through the aggregate. To this end the cross-sectional area of the aggregate layer should be equal to or smaller than that of the pouring port or the discharger port. Where there is a restricted portion between the aggregate layer and the pouring port, such portion manifests a nozzle like resistance against the poured fluid thus affecting the result of measurement. In the embodiments shown in FIGS. 3, 4, 5, 8 and 9, the bent portion of the tube affords a slight resistance to the flow of the plastic material so that the result of measurement varies more or less according to the property of the bent portion. For this reason, it is essential to use the same measuring device for the fluids of the same group. Where it is necessary to compare the results obtained by different measuring devices it is necessary to eliminate the resistance at the bent portion. Furthermore, in the case as shown in FIG. 3 or 5, the solid particles in the plastic fluid may deposite on the bottom of the tube and the deposited particles may be sent to the aggregate layer thereby increasing its flow resistance.

The embodiments shown in FIGS. 10, 11 and 12 are designed to eliminate this difficulty. In the embodiment shown in FIG. 10, the inlet leg 11 and the outlet leg 12 are interconnected through a horizontal leg 13 at portions slightly above the bottom, thereby forming flow resistance reduction parts 11a and 12a beneath the horizontal leg 13. These parts reduce the flow resistance at the curved portions to the flow of the fluid so that measurement values will not be influenced by using a curved tube. In the embodiment shown in FIG. 11, the inlet and outlet legs are connected together through a chamber 14 having a relatively large volume. In the case shown in FIG. 10, the aggregate 2 is contained in the horizontal leg 13 whereas in the embodiment shown in FIG. 11, in leg 16. As shown in FIG. 11, internal diameter D of the leg 15 and $D_2$ of the chamber 14 should be equal or more than $D_1$ of the aggregate packed portion in leg 16. In the embodiment shown in FIG. 12, one leg 20 is connected to the upper side 18 and the other leg 20a is bent and connected to the side 19 of a chamber 17 having a relatively large volume. In the embodiments shown in FIGS. 11 and 12, chambers 14 and 17 have sufficient internal diameters so that there is no fear of increasing the flow resistance by the deposited solid particles. Even when the plastic fluid solidifics on the aggregate it is easy to dismount the leg containing the aggregate so as to clean or exchange the same.

In each of the embodiments shown in FIGS. 3–12, a static head difference h is created between the levels of the fluid in two legs (In FIGS. 6–9, fluid surface in tank can be considered as the level of the fluid in one leg). At the time of pouring the plastic fluid, the level in the pouring side is higher than that shown in the drawing but this level gradually lowers as the poured fluid flows into the outlet leg through the packed aggregate 2. Of course such static head difference h is created by the presence of the packed aggregate and differs dependent upon the characteristics of the aggregate, and the poured plastic fluid. Accordingly, it is possible to determine the shear stress yielding value of the plastic fluid for the aggregate by the static head difference h. Thus, $$Fo = (\delta h/l)$$

where Fo represents the shear stress yielding value in $g/cm^3$ for the aggregate, $\delta(g/cm^3)$ the specific gravity of the fluid and l(cm) the length of the packed aggregate layer.

In the following, one example of the measurement is illustrated. A concrete mortar was prepared by admixing sand and cement at a ratio of 1:1, 43% of water based on the weight of cement and 1.3% of a dispersion agent. The mortar had a specific gravity of 2.1 $g/cm^3$. Three measuring devices as shown in FIG. 3 were prepared and glass beads having a diameter of 20 mm was packed over a length of 10, 15 and 20 cm respectively. The mortar was poured into the measuring devices and the static head difference was measured in each case. The measured static head differences are shown in the following Table 1.

Table 1

| length of reference aggregate packed | immediately after compounding | after 30 min. | after 60 min. |
|---|---|---|---|
| 20 cm | 7.5 cm | 8.0 cm | 15.1 cm |
| 15 cm | 6.1 cm | 6.5 cm | 10.4 cm |
| 10 cm | 4.8 cm | 5.0 cm | 7.9 cm |

As can be noted from this table, the static head difference varies in direct proportion to the 5 cm variation in the length of the packed aggregate thus accurately showing the pouring characteristic of the mortar.

It will thus be noted that the pouring can be performed by determining the required pouring condition by utilizing the static head difference shown in Table 1. Where the static head difference is obtained by using the passage having a length of 15 cm, and the aggregate packed therein comprising glass beads having a diameter of 20 mm it is possible to smoothly pour the fluid by preparing a cement mortar or a cement paste such that the static head difference will be included in a range of 30 to 200 mm and by determining the pouring condition by converting the characteristic of the aggregate packed in the mould into the characteristic of the reference aggregate.

In the case shown in Table 1, the pressure necessary for the initial shear stress when a mortar is poured into a flat mould having a length of 4 m and packed with an aggregate having the same void condition as said glass beads, 30 minutes after preparation of the mortar is calculated by the following equation $$\{(6.5-5.0) \div 5 \times 400 + 5 - 2(6.5-5)\} \times 2.1 = 256 \text{ g/cm}^2$$

When the mortar is poured 60 minutes after preparation the required pressure is $$\{(10.4-7.9) \div 400 + 7.9 - 2(10.4-7.9)\} \times 2.1 = 342 \text{ g/cm}^2$$

In the latter case, the difference between the packed aggregate length of 10 cm and 15 cm is substantially smaller than the difference between the packed aggregate length of 15 cm and 20 cm. This means that as the length of the packed aggregate increases, the pouring pressure for the shear stress yielding value increases greatly. In such a case, it is expected that the pouring pressure would be much larger than the value 342 g/cm$^2$ calculated as above described.

As above described, according to the measuring device of the present invention it is also possible to measure at the same time the resistance of the aggregate packed in the mould caused by the deposited solid particles. More particularly, when pouring the plastic fluid such as a cement mortar into the interstices between coarse aggregate the solid component or particles of the mortar accumulate between the aggregates thereby increasing the flow resistance with time. With the measuring device of this invention it is also possible to readily determine such flow resistance as well as the pouring pressure required to overcome it. This can be accomplished by measuring the static head difference required to calculate the initial shear stress and after passing a predetermined quantity of the plastic fluid through the packed aggregate layer by measuring again the head difference. In this case, the latter static head difference is always larger than the former static head difference so that it is possible to determine the pressure required for overcoming the flow resistance caused by the deposited solid particles in accordance with the relationship between the variation in the static head difference and the quantity of the plastic fluid passing through the aggregate.

Moreover, according to the present invention, it is also possible to measure the pouring speed, that is the fluidity. Thus, with the discharge port of the measuring device closed by a plug or a lid, not shown a predetermined quantity of the plastic fluid is poured into the measuring device through the pouring port to create a definite level difference. Then, the plug is removed to allow the plastic fluid to flow and the time required for a definite quantity of the fluid to pass through the packed aggregate is measured. Then the pouring speed can be calculated from the cross-sectional area and the length of the packed aggregate, said definite flow quantity and the time.

The capability of measuring the initial shear stress yielding point, the pouring pressure for overcoming the flow resistance caused by the deposited solid particles as well as the pouring speed by the same measuring device is extremely convenient in the field work. In other words, this means that it is possible to simultaneously obtain two values by a single operation which is important for the field work because it is extremely difficult to prepare absolutely identical cement mortars or the like.

In connection with the measurement of the three elements described above, that is the relative initial shear stress, the relative closure coefficient and the relative flow viscosity coefficient we propose a novel measuring device as diagrammatically shown in FIG. 13. The measuring device shown in FIG. 13, comprises a vertical leg 21 provided with a pouring port at its upper end, a horizontal connecting leg 22 and a short vertical leg 23 containing a suitable aggregate 26 packed between metal wire nets 25. The legs 21, 22 and 23 are made of tubes having a circular or square cross-sectional configuration. The leg 21 has a sufficient length to form a required static head difference necessary to create a pressure for causing the plastic fluid to flow. Advantageously, the inner diameter of the leg 23 should be equal to or smaller than that of the legs 21 and 22. Also it is desirable to form chambers or accumulators 24 at both ends of the connecting leg 22 for the reason described above.

Of course, the legs 21, 22 and 23 may be formed by a single length of the tube in the same manner as the embodiment shown in FIG. 3. The detail of the construction of the measuring device shown in FIG. 13 and the modification thereof will now be described in connection with FIGS. 14 through 17.

In the embodiment shown in FIGS. 14 and 15, the vertical leg 21 is graduated with a scale 31 and the connecting leg 22 is made of three sections. The aggregate 26 is packed between metal wire nets 25 and contained in the middle section 33. The connecting leg 22 has a U shaped configuration and an overflow tube 27 is connected to the righthand section. The assembly is mounted on a base 28. A drain pipe 32 including a cock 35 is connected to the righthand section of the connecting tube for discharging the plastic fluid remaining in the measuring device after completion of the measurement. A cover 29 operated by a handle 34 is provided for the upper end of the discharge tube 27 for normally closing the same. An annular reciever 38 provided with a discharge chute 37 is provided to surround the overflow tube 27. The leg 21 and the overflow tube 27 are connected together by removable coupling members 39. Opposed channel shaped guide members 36 are secured to the base 28 for guiding the opposed vertical sections of the connecting leg 22. This construction permits removal of either one of the vertical sections for the purpose of cleaning or exchanging the packed aggregate 26. If desired, the overflow tube 27 may be omitted to cause the plastic fluid to overflow through the upper opening of the righthand section of the connecting tube, in which case the cover 29 is lowered along guide rods 40 mounted on the base 28. In exchanging the packed aggregate 26, the fresh aggregate shoudl have the same length as the original length. If desired, a middle section 33 having a different length may be substituted for by removing either one of the vertical sections.

FIG. 16 shows a modification in which a portion of the embodiment shown in FIGS. 14 and 15 has been varied. More particularly, a pressure applying mechanism 41 is added to the pouring leg 21. Thus, a pipe 42 from a pressurized air tank 41 is connected to a pressurizing cylinder 43 added to the upper end of the tube 21.

In the embodiment shown in FIGS. 13 to 15, in order to create a sufficiently large static head difference it is necessary to increase the length of the tube 21, which is inconvenient to handle in the field. When pressurized air is used as shown in FIG. 16, it is possible to increase the static head difference or the pressure to move the plastic fluid. Although in the embodiments shown in FIGS. 13 through 16 it is necessary to sample a definite quantity of the plastic fluid prepared for the practical use. The embodiment shown in FIG. 17 is designed to eliminate such inconvenience. Thus, the measuring device is directly attached to the tank of a concrete mixer 50 through a valve 44. The measuring device comprises two vertical tubes 51 and 53 and a pressure applying mechanism 41 is connected to the upper end of the tube 51 in the same manner as in FIG. 16. The righthand tube 53 is provided with a cover 29 operated by an operating cylinder 45 and a chute 37 for receiving the overflown concrete. A pressure differential transmitter 46 is provided at the bottom of the tube 51 for detecting and transmitting the pressure condition therein to automatically control the pouring operation as will be described later. A water tube 47 including a valve 48 is connected to the bottom of the measuring device for the purpose of removing the concrete mortar remaining after completion of the measurement.

In the embodiments shown in FIGS. 13 through 17 the static head difference creating means and the pressurizing mechanism were incorporated into the lefthand tube and the measuring device was constructed to have a L or U shaped form, but if desired, the elements of the measuring device may be arranged along a straight line thus simplifying the construction and making easy to measure plastic fluids having a high viscosity. In such a linear construction, the pouring port and the pressurizing mechanism may be provided either above or beneath the rod shaped structure.

In the embodiments shown in FIGS. 13 to 17, the section 23 or 33 or 53 is packed with a coarse aggregate actually used in the field or a model aggregate and the packed length is L as shown in FIG. 13. The cement mortar or paste is poured into the tube 21 or 51 and flows as shown by arrows in FIG. 13 to pass through the aggregate. When the poured plastic fluid begins to overflow the pouring is stopped. Thereafter, the level in the pouring tube lowers gradually and comes to stop thus creating a definite static head or level difference $H_1$. This static head difference corresponds to the relative initial shear stress determined by the aggregate or the condition of the flow passage and expressed in centimeters or $g/cm^3$. Thereafter, the discharge port is closed by the cover and a predetermined quantity of the same plastic fluid is poured into the tube 21 to a level 1 to form a static head difference. Then the cover or plug is removed to permit the fluid to overflow. During this process, the time required for the level of the fluid passes successively through positions $l_1, l_2 \ldots l_n$ is measured thus determining the distances between adjacent positions and the times $t_1, t_2 \ldots t_n$. Even when the distances are equal the time increases gradually. Finally, the level of the fluid reaches a position creating a static head difference $H_2$ which is larger than the initial static head difference $H_1$. The relative flow viscosity coefficient ($g.sec/cm^3.cm$) can be determined by the relationship among $l_1, l_2 \ldots l_n$ and the $t_1, t_2 \ldots t_n$, and the relative closure coefficient can be determined from the initial and final static head differences $H_1$ and $H_2$. Denoting now that $Fo_1$ (g/cm$^3$): relative shear stress yielding value for static head difference $H_1$,
$Fo_2$ (g/cm$^2$): relative shear stress yielding value for static head difference $H_2$,
$\lambda$(g.sec/cm$^3$. cm): relative flow viscosity coefficient,
$\Delta Fo$ (g/cm$^3$. cm): relative closure coefficient,
$U_f$(cm.sec): hollow column speed described above
$Ua$ (cm/sec): apparent speed (pouring speed)
$\epsilon$: percentage of the aggregate void described above,
$\rho$ (g/cm$^3$): weight of the unit volume of the plastic fluid,
$Pu$ (g/cm$^3$): velocity head,
$L$ (cm): length of the aggregate layer,
$Q$ (g/cm$^3$): quantity of the fluid passing through,
$A$ (cm$^2$): the cross-sectional area of the aggregate layer, then values of $Fo_1$, $Fo_2$, $\Delta Fo$, $\lambda$, $Pu$, $U_f$ and $Ua$ can be determined as follows:

$$Fo_1 = \frac{H_1 \rho}{L}$$

$$Fo_2 = \frac{H_2 \rho}{L^2}$$

$$\Delta Fo = \frac{(H_2 - H_1)\rho}{L(l - H_2)} = \frac{(Fo_2 - Fo_1)A}{QL}$$

$$\lambda = \frac{Pu}{U_f}$$

$$Pu = \frac{(\frac{l_1}{2} + l_2)\rho}{L} - Fo_2 - \Delta Fo \, l_1, l_2 \ldots l_n$$

where
$l_z = l_1 (l_1, l_2 \ldots l_n)$
$U_f = l_1/t_1$
$Ua = U_f/\epsilon$

We have found a new fact as a result of variously varying the factors regarding the flow of the fluid as well as the factors of the fluid itself and carefully analyzing combination of such factors. Thus, where the plastic fluid comprises a concrete mortar, various types of the plastic fluid as shown in Table 2 were prepared in which the fineness modulus (F.M) of the sand used was varied. The results of measurement are shown in the following Table 3.

Table 2

| Sample no. | quantity | cement Kg | dry river sand Kg | dispersion agent (l) | effective water Kg | W/C % | F.M. |
|---|---|---|---|---|---|---|---|
| 1-1 | one batch | 14 | 13.2 | 0.140 | 5.81 | 41.5 | 1.13 |
|  | 1 m$^3$ | 892 | 841 | 8.92 | 370 |  |  |
| 1-2 | one batch | 14 | 13.6 | 0.140 | 5.81 | 41.5 | 1.45 |
|  | 1 m$^3$ | 892 | 866 | 8.92 | 370 |  |  |
| 1-3 | one batch | 14 | 14.4 | 0.140 | 5.81 | 41.5 | 1.54 |
|  | 1 m$^3$ | 863 | 888 | 8.63 | 358 |  |  |
| 1-4 | one batch | 14 | 142 | 0.140 | 5.81 | 41.5 | 1.79 |
|  | 1 m$^3$ | 881 | 398 | 8.81 | 366 |  |  |
| 1-5 | one batch | 14 | 13.7 | 0.140 | 0.140 | 5.81 | 2.33 |
|  | 1 m$^3$ | 892 | 873 | 8.92 | 370 |  |  |

Table 3

| Sample number | F.M. | Fo g/cm$^3$ | $\lambda$ g . sec/cm$^4$ | $\Delta Fo \times 10^{-3}$ g/cm$^4$ | flow value sec. |
|---|---|---|---|---|---|
| 1-1 | 1.13 | 3.24 | 2.28 | 10.7 | 72.4 |

Table 3-continued

| Sample number | F.M. | Fo g/cm³ | λ g·sec/cm⁴ | ΔFo × 10⁻³ g/cm⁴ | flow value sec. |
|---|---|---|---|---|---|
| 1-2 | 1.45 | 4.32 | 1.65 | 7.9 | 65.9 |
| 1-3 | 1.54 | 0.85 | 1.01 | 2.7 | 26.0 |
| 1-4 | 1.79 | 1.68 | 1.40 | 4.8 | 27.6 |
| 1-5 | 2.33 | 1.85 | 1.08 | 6.1 | 24.0 |

The manner of varying these data is complicated. Thus, with regard to sample 1-3 in which F.M = 1.54 the values of Fo, λ and ΔFo are low, but in sample 1-2 having nearly the same value of F.M = 1.45, the values of Fo, λ and ΔFo are different greatly, and these values also vary greatly for other samples. The manner of such variation is quite different from that of the measured value (the flow value which represents the time in sec. required for a definite quantity of the plastic fluid to discharge through an opening at the bottom of the funnel shaped measuring device) obtained by using a P funnel (Japanese Institute of Architecture JASS. ST-701) which is used to measure the fluidity of concrete mortar or the like.

Such complicated variations also occur when the ratio of water to cement and the ratio of sand to water are varied. The following Table 4 shows examples of the composition of concrete mortar in which the water to cement ratio W/C and the sand to cement ratio (C/S) are varied over a wide range and the results of measurement of the plastic fluids having the compositions shown in Table 4 are shown in the following Table 5 from which it can be noted that the values of Fo, λ and flow value decrease as the water to cement ratio increases whereas the ΔFo varies irregularly. The cement to sand ratio has generally some relation with respect to the flow value but other factors vary irregularly.

Table 4

| Sample number | water to sand ratio | water to cement ratio % | Composition per m³ | | |
|---|---|---|---|---|---|
| | | | cement Kg | dry river sand Kg | dispersion agent l | effective water Kg |
| 2-1-1 | 1/0.8 | 33.5 | 989 | 817 | 9.89 | 332 |
| 2-1-2 | " | 35 | 982 | 812 | 9.82 | 344 |
| 2-1-3 | " | 36.5 | 966 | 798 | 9.66 | 353 |
| 2-1-4 | " | 38 | 950 | 786 | 9.50 | 361 |
| 2-1-5 | " | 39.5 | 942 | 779 | 9.42 | 372 |
| 2-2-1 | 1/1 | 38.5 | 878 | 903 | 8.78 | 333 |
| 2-2-2 | " | 40 | 870 | 895 | 8.70 | 348 |
| 2-2-3 | " | 41.5 | 863 | 888 | 8.63 | 358 |
| 2-2-4 | " | 43 | 853 | 878 | 8.53 | 367 |
| 2-3-1 | 1/1 | 37 | 887 | 913 | 8.87 | 328 |
| 2-3-2 | " | 38.5 | 878 | 903 | 8.78 | 338 |
| 2-3-3 | " | 40.5 | 863 | 888 | 8.63 | 350 |
| 2-3-4 | " | 42.5 | 853 | 877 | 8.53 | 363 |
| 2-3-5 | " | 44.5 | 834 | 858 | 8.34 | 371 |
| 2-4-1 | 1/1.2 | 42 | 803 | 997 | 8.03 | 338 |
| 2-4-2 | " | 43.5 | 796 | 988 | 7.96 | 347 |
| 2-4-3 | " | 45 | 781 | 969 | 7.81 | 352 |
| 2-4-4 | " | 46.5 | 775 | 962 | 7.75 | 361 |

Table 5

| Sample no. | Fo g/cm³ | λ g·sec/cm⁴ | ΔFo ×10⁻³ g/cm⁴ | flow value sec. | weight of unit volume Kg/l | temp. after compounding °C. |
|---|---|---|---|---|---|---|
| 2-1-1 | 1.34 | 2.68 | 5.0 | 74.0 | 2.137 | 26.2 |
| 2-1-2 | 0.82 | 1.73 | 0.8 | 42.2 | 2.137 | 26.3 |
| 2-1-3 | 0.09 | 1.12 | 1.8 | 27.8 | 2.117 | 26.4 |
| 2-1-4 | 0.73 | 0.86 | 0.3 | 24.2 | 2.097 | 27.0 |
| 2-1-5 | 0.19 | 0.63 | 0.3 | 18.0 | 2.092 | 25.9 |
| 2-2-1 | 1.81 | 1.83 | 4.8 | — | 2.118 | 27.3 |
| 2-2-2 | 1.13 | 1.29 | 1.6 | — | 2.113 | 26.0 |
| 2-2-3 | 0.81 | 1.01 | 0.7 | — | 2.108 | 26.5 |
| 2-2-4 | 0.83 | 0.83 | 0 | — | 2.098 | 26.0 |
| 2-3-1 | 3.05 | 2.58 | 8.8 | 83.8 | 2.128 | 26.0 |
| 2-3-2 | 2.08 | 1.73 | 3.1 | 41.0 | 2.119 | 26.0 |
| 2-3-3 | 1.02 | 1.16 | 3.1 | 28.4 | 2.100 | 26.0 |
| 2-3-4 | 0.81 | 0.86 | 3.4 | 24.0 | 2.093 | 25.5 |
| 2-3-5 | 0.55 | 0.60 | 1.6 | 17.6 | 2.003 | 25.0 |
| 2-4-1 | 3.14 | 1.81 | 5.4 | 53.7 | 2.138 | 27.2 |
| 2-4-2 | 1.42 | 1.29 | 0.5 | 32.4 | 2.135 | 26.5 |
| 2-4-3 | 1.16 | 1.03 | 1.0 | 26.4 | 2.102 | 26.0 |
| 2-4-4 | 0.63 | 0.76 | 0.4 | 20.1 | 2.098 | 26.0 |

Table 6 below shows compositions in which the quantity of the dispersion agent is varied together with the water to cement ratio and the results of measurements are shown in Table 7 which shows that ΔFo varies in a complicated manner.

Table 6

| Sample number | dispersion agent used %/ cement | water to cement ratio % | Composition per m³ | | |
|---|---|---|---|---|---|
| | | | cement Kg | dry river sand Kg | dispersion agent (l) | effective water Kg |
| 3-1-1 | 0 | 54 | 776 | 801 | 0 | 419 |
| 3-1-2 | " | 56 | 760 | 785 | 0 | 426 |
| 3-1-3 | " | 58 | 760 | 785 | 0 | 441 |
| 3-1-4 | " | 60 | 742 | 767 | 0 | 445 |
| 3-2-1 | 0.5 | 45.5 | 837 | 863 | 4.18 | 381 |
| 3-2-2 | " | 47 | 826 | 851 | 4.13 | 388 |
| 3-2-3 | " | 48.5 | 807 | 832 | 4.03 | 392 |
| 3-2-3 | " | 50 | 803 | 828 | 4.01 | 401 |
| 3-3-1 | 1.0 | 37 | 887 | 913 | 8.87 | 328 |
| 3-3-2 | " | 38.5 | 878 | 903 | 8.78 | 338 |
| 3-3-3 | " | 40.5 | 863 | 888 | 8.63 | 350 |
| 3-3-4 | " | 42.5 | 833 | 877 | 8.53 | 363 |
| 3-3-5 | " | 44.5 | 854 | 858 | 8.34 | 371 |
| 3-4-1 | 1.5 | 34 | 890 | 916 | 13.4 | 303 |
| 3-4-2 | " | 35.5 | 890 | 916 | 13.4 | 316 |
| 3-4-3 | " | 37 | 886 | 911 | 13.3 | 328 |
| 3-4-4 | " | 38.5 | 881 | 906 | 13.2 | 339 |
| 3-4-5 | " | 40 | 863 | 888 | 13.0 | 345 |

Table 7

| Sample no. | Fo g/cm³ | λ g·sec/cm⁴ | ΔFo ×10⁻³ g/cm⁴ | flow value sec. | weight of unit volume Kg/l | temp. after compounding °C. |
|---|---|---|---|---|---|---|
| 3-1-1 | 4.44 | 0.90 | 3.2 | 25.0 | 1.997 | 26.0 |
| 3-1-2 | 3.50 | 1.06 | 11.0 | 22.0 | 1.972 | 25.7 |
| 3-1-3 | 2.15 | 0.71 | 8.8 | 15.2 | 1.985 | 25.7 |
| 3-1-4 | 2.37 | 0.54 | 4.7 | 14.6 | 1.955 | 25.6 |
| 3-2-1 | 4.56 | 1.11 | 10.0 | 27.8 | 2.080 | 27.4 |
| 3-2-2 | 2.76 | 0.97 | 6.8 | 19.0 | 2.065 | 28.0 |
| 3-2-3 | 2.23 | 0.83 | 4.5 | 16.0 | 2.030 | 27.8 |
| 3-2-4 | 1.39 | 0.51 | 2.0 | 14.2 | 2.032 | 27.0 |
| 3-3-1 | 3.05 | 2.58 | 8.8 | 83.8 | 2.128 | 26.0 |
| 3-3-2 | 2.08 | 1.73 | 3.1 | 41.0 | 2.119 | 26.0 |
| 3-3-3 | 1.02 | 1.16 | 3.1 | 28.4 | 2.100 | 26.0 |
| 3-3-4 | 0.81 | 0.86 | 3.4 | 24.0 | 2.093 | 25.5 |
| 3-3-5 | 0.55 | 0.60 | 1.6 | 17.7 | 2.063 | 25.0 |
| 3-4-1 | 0.73 | 4.75 | 3.1 | 113.8 | 2.122 | 27.0 |
| 3-4-2 | 0.30 | 2.51 | 2.4 | 57.5 | 2.135 | 26.3 |
| 3-4-3 | 0.14 | 1.30 | 1.8 | 39.0 | 2.133 | 26.5 |
| 3-4-4 | 0.06 | 1.16 | 2.3 | 29.8 | 2.125 | 26.0 |
| 3-4-5 | 0.05 | 0.89 | 1.5 | 23.5 | 2.096 | 26.0 |

Even with the same composition, the fluidity of the plastic fluid varies greatly depending upon such factors as the water content of the sand, the order of compounding the ingredients, and the interval of compounding. We have used sand having a water content between 4.38% (dry state) and 40% to prepare cement mortars in which W/C = 43% and the ratio C/S is substantially equal. The results of measurement made on these mortars are shown in the following Table 8 in which symbol "a ↑" shows that the mortar was passed upwardly through the packed aggregate layer, whereas symbol "b ↓" shows that the mortar was passed downwardly through the aggregate layer. In any case, variation in the measured values is complicated. Generally speaking, sand having a water content of 6–26% shows a high value of Fo but water content of 40%, that is, above 28–35% also shows a high value of Fo. However, flow value obtained by using P funnel varies in a considerably different manner from the before-mentioned.

All products moulded from the mortars shown in Table 8 have a compression strength of higher than 400 Kg/cm². More particularly, when the water content of the sand is less than 6%, the compression strength is less than 420 Kg/cm², on the other hand, when the water content of the sand ranges from 9 to 25%, the compression strength ranges from 460 Kg/cm² to 484 Kg/cm². But when the water content of the sand reaches 26%, the compression strength rapidly decreases to 423 Kg/cm² and at 30%, 32%, 35% and 40% the compression strength is 532 Kg/cm², 462 Kg/cm², 530 Kg/cm² and 550 Kg/cm² respectively. The bending strength generally ranges between 70 and 80 Kg/cm² but for the water content of 35–40%, the bending strength is about 90 Kg/cm².

Table 9

| Sample number | symbol | water content % | flow value A sec. | B sec. | Fo mm | weight of unit vol. Kg/m³ |
|---|---|---|---|---|---|---|
| 1 | SC+W | 3.41 | 19.2 | 30.0 | 12 | 1.903 |
| 2 | ⓈC+W | 20.48 | 15.4 | 26.8 | 30 | 2.070 |
| 3 | WS+C | 3.41 | 26.8 | 67.4 | 174 | 2.055 |
| 4 | WⓈ+C | 20.48 | 27.2 | 60.8 | 160 | 2.047 |
| 5 | WC+S | 3.41 | 20.9 | 40.1 | 127 | 2.061 |
| 6 | WC+Ⓢ | 20.48 | impossible | impossible | impossible | 2.060 |
| 7 | SC+W | 3.20 | 20.8 | 31.8 | 0 | 2.112 |

Table 10

| Sample number | symbol | water content | flow value A sec. | B sec. | Fo mm | weight of unit vol. Kg/m³ |
|---|---|---|---|---|---|---|
| 1 | SC + W | 3.31 | 17.8 | 32.6 | 90 | 2.025 |
| 2 | ⓈC + W | 16.01 | 31.4 | impossible | 180 | 1.979 |
| 3 | WS + C | 3.31 | 21.6 | " | 150 | 1.997 |
| 4 | WⓈ + C | 16.01 | 27.0 | " | 190 | 1.997 |
| 5 | WC + S | 3.31 | 17.6 | 31.7 | 145 | 1.998 |
| 6 | WC + Ⓢ | 16.01 | 20.0 | impossible | 160 | 1.980 |
| 7 | ⓈC + W | 16.01 | 22.0 | " | 190 | 1.952 |

As can be noted from these tables even with the same composition, the fluidity of the mortar varies greatly as well as the weight per unit volume. The fact that the characteristics of the mortar are greatly influenced by Table 8

| Sample Number | water content in sand % | Sand Kg | compensated composition | | | Fo m/m . g | | P funnel flow value sec. | weight per unit volume Kg/m³ | rate of breezing | | |
|---|---|---|---|---|---|---|---|---|---|---|---|---|
| | | | water of compounding l | dispersion agent c. c. | surface water of sand l | a ↑ m/min | b ↓ m/min | | | 30 min. | 1 hr. | 2 hrs. |
| 1 | 40 | 15.648 | 0.300 | 150 | 5.352 | 122 m/m 1.25 g | 140 m/m 1.44 g | 76.0 | 2.050 | 0 | 0.13 | 0.10 |
| 2 | 35 | " | 1.050 | " | 4.602 | 92 0.96 | 95 0.99 | 53.4 | 2.088 | 0.50 | 0.88 | 1.38 |
| 3 | 30 | " | 1.800 | " | 3.852 | 75 0.78 | 90 0.94 | 45.0 | 2.080 | 0.13 | 0.40 | 0.68 |
| 4 | 25 | " | 2.550 | " | 3.102 | 135 1.37 | 160 1.62 | 53.8 | 2.030 | 0.14 | 0.24 | 0.30 |
| 5 | 18 | " | 3.600 | " | 2.052 | 140 1.41 | 160 1.62 | 50.0 | 2.020 | 0 | 0 | 0 |
| 6 | 15 | 15.473 | 4.050 | " | 1.777 | 123 1.26 | 140 1.43 | 41.5 | 2.048 | " | " | " |
| 7 | 12 | " | 4.500 | " | 1.327 | 113 1.14 | 140 1.42 | 42.0 | 2.023 | " | " | " |
| 8 | 7 | " | 4.950 | " | 0.877 | 100 1.02 | 135 1.38 | 48.3 | 2.038 | " | " | " |
| 9 | 6 | " | 5.400 | " | 0.427 | 107 1.08 | 142 1.43 | 59.0 | 2.013 | " | " | " |
| 10 | 3 | 15.150 | 6.000 | " | 0.300 | 45 0.45 | 57 0.57 | 41.8 | 2.000 | foam 2 m/m | foam 3 m/m | — |
| 11 | 1 | " | 6.300 | " | 0 | 50 0.10 | 60 0.60 | 53.8 | 1.980 | foam 3 m/m | foam 4 m/m | — |
| 12 | absolutely dry | 14.343 | 6.957 | " | 0 | 48 0.48 | 75 0.75 | 90.3 | 1.980 | 0.2 | 0.5 | 0.9 |

The order of compounding the ingredients was varied as shown in Tables 9 and 10. In Table 9 the ratio W/C was 45% and 1% of the dispersion agent was added. Table 10 shows plain mortars not incorporated with any dispersion agent. In these tables symbol Ⓢ shows a case wherein the water content of the sand is relatively high, for example 20.48% or 16.01%, whereas Ⓢ shows a case wherein the water content is relatively low, for example 3.41% or 3.31%. Compounding was effected such that after kneading for 3 minutes the ingredient shown on the lefthand side of the symbol column, the ingredient shown in the righthand side was added and kneaded for 4 minutes.

the water content of the sand and by the order of incorporation of the ingredients has not been recognized. These facts are advantageously used in the field as relative guantitative date. 7 days after moulding the mortars shown in Tables 9 and 10, the compression strength and the bending strength of the products were measured. The compression strength generally ranges between 230 and 400 Kg/cm² but in some cases ranges between 360 and 392 Kg/cm² and varies slightly. In another cases the compression strength is relatively low, that is between 225 and 350 Kg/cm² and varies in a wide range. The same is true for the bending strength. Thus, in certain cases, ranges between 66 and 74 Kg/cm² and varies slightly and in another cases ranges between 50 and 65 Kg/cm² and varies greatly. Accordingly, these factors play important rolls in determining the quality of the products.

Furthermore, the fluidity of the mortar varies greatly depending upon the compounding time. For example, in a mortar having a composition comprising 50 Kg of cement, 56.2 Kg of sand having a water content of 11.11%, water 15.5 l and 500 cc of a dispersion agent, at first the cement and the sand were compounded for 3 minutes at a dry state, then water and the dispersion agent were incorporated over an interval of 18 seconds, and 15 seconds after such incorporation the compounding operation was started. Table 11 below shows the relationship between the compounding time and the fluidity of the resulting mortar.

Table 11

| compounding time | 15 sec | 30 sec | 45 sec | 1 m 30 sec | 3 min |
|---|---|---|---|---|---|
| flow value A | 56.0 | 54.6 | 63.0 | — | 95.0 |
| flow value B | 95.8 | 92.2 | 121.6 | — | — |
| Fo mm | 155 | 150 | impossible | impossible | impossible |

According to this invention, flow value is measured by using the special flow cone which has a upper portion mounted on a standard flow cone, the capacity of said upper portion being same as that of the standard flow cone. Flow value (A) indicates the time the fluid in the lower portion, i.e. the standard flow cone is flowed out so that the fluid in the upper portion is flowed down into the lower portion. Flow value (B) indicates the time the fluid flowed down into the lower portion from the upper portion is flowed out, which is consistent with a standard flow value.

This table shows that up to a certain time the fluidity is improved but degrades thereafter.

Another mortar was prepared by the same method of compounding as above described but by using a composition consisting of 50 Kg of cement, 52.6 Kg of sand containing 3.95% of water, 19.1 l of water and 500 cc of a dispersion agent. Table 12 below shows the relationship between the fluidity and the compounding time of this mortar.

Table 12

| compounding time | 15 sec | 30 sec | 45 sec | 1. min | 1.5 min | 3 min | 5 min |
|---|---|---|---|---|---|---|---|
| flow value A | 58.0 sec | 55.0 | 51.8 | 52.3 | 54.8 | 57.6 | 69.6 |
| flow value B | 93.6 | 78.0 | 74.4 | 72.9 | 70.4 | 76.4 | 109.4 |
| Fo, mm | 64 | 37 | 32 | 43 | 57 | 126 | 155 |

This table also shows that up to a certain time the fluidity is improved but degrades thereafter.

The same tendency was confirmed with reference to various compounds containing alumina cement or clay and utilized to prepare refractries. Table 13 below shows some results of measurement of the fluidity of a refractory.

Table 13

| W/C % | AlC:S | weight of unit volume Kg/cm$^3$ | P funnel sec. | Fo(g/cm$^3$) 1 | Fo(g/cm$^3$) 2 | (g/cm$^4$) ΔFo | $U_f$ cm/sec | λ | compression strength |
|---|---|---|---|---|---|---|---|---|---|
| 32.0 | 1:0 | 2.025 | 16.5 | 1.27 | 1.32 | 0.008 | 0.48 | 4.6 | 421 |
| 32.3 | 1:0.2 | 2.045 | 17.0 | 0.97 | 0.81 | −0.0058 | 0.41 | 2.7 | 428 |
| 33.4 | 1:0.4 | 2.210 | 47.0 | 2.76 | 2.65 | −0.0027 | 0.13 | 9.7 | 666 |
| 38.6 | 1:0.6 | 2.165 | 27.0 | 1.84 | 1.84 | −0.0086 | 2.22 | 9.3 | 489 |

In this table, AlC represents alumina cement, S sand of SK 38, and Cl clay. As the resistance element of the measuring device was used a tube packed with chamotte having a particle size of 10 to 15 mm for a length of 20 cm.

From the foregoing description it can be noted that the fluidity of the plastic fluid is delicately influenced by the order of incorporation of the ingredients, water content, conditions of compounding, etc., that the flow is influenced by the shape of the flow passage, characteristics and the void factor of the packed aggregate, and that Fo is influenced by the directions of flow (a ↑ and b ↓). Thus, the fluidity, flow and Fo can not be judged qualitatively or conceptionally.

To make more clear the nature of the fluidity which varies in a complicated manner we have made experiments by using a mould having a pour length of 2 to 4 meters and packed with various aggregates and compared the results of these experiments with the results obtained by the measuring devices as shown in FIG. 13 through 17. As a consequence, we have found that the pressure loss P required to pour mortar or paste into the actual mould can be expressed for example by the following equation.

$$P = \sqrt{\frac{X}{X - \int_0^t U_f^2 \, df}} \, (Fo + \lambda \, U_f) \int_0^t U_f \cdot dt \cdot \frac{1}{\epsilon} + \rho h \quad \text{I}$$

where h represents the height of a member to be poured, and X, Fo and λ are determined as follows $$X = \frac{C_2}{\sqrt{C_0 \cdot C_1}} \cdot \frac{1}{\sqrt{\Delta Fo}} \quad \text{II}$$

$$Fo = C_0 \cdot C_1 \cdot Fo_1 \quad \text{III}$$

$$\lambda = C_0 \cdot C_1 \cdot \lambda_1 \quad \text{IV}$$

where
$C_0$: characteristic value of the measuring device as shown in FIGS. 13-15
$C_1$: correction factor between the measuring device and the aggregate packed in an actual mould
$C_2$: coefficient determined by the shape and dimension of the mould Where other physical factors should be taken into consideration these equations are suitably modified.

In the case of a constant speed pouring equation I can be modified to the following equation V or VI.

$$P = \sqrt{\frac{T}{T - t}} \, (Fo + \lambda \, U_f) \, \frac{U_f t}{\epsilon} + \rho h \quad \text{V}$$

where T represent the maximum pouring time and is expressed by $$T = \frac{X}{U_f^2} \qquad \text{VI}$$

$$P = \sqrt{\frac{L_{max}}{L_{max} - L}} (Fo + \lambda U_f L) + \rho h$$

where $L_{max}$ represents the maximum pouring distance and is expressed by $$L_{max} = \frac{U_f T}{\epsilon} = \frac{X}{U_f \epsilon}, \text{ and}$$

$$L = \frac{U_f t}{\epsilon}$$

In the case of the constant speed pouring the speed $U_f$ required to pour the plastic fluid under a pressure of P (g/cm$^2$) over a distance of L (cm) is given by the following equation.

$$U_f = \frac{\Delta P \sqrt{4 \times LFo\lambda\epsilon + \Delta P^2 \epsilon^2 + 4X^2\lambda^2 - 2XLFo\lambda} - \Delta P^2 \epsilon}{2XL\lambda^2} \qquad \text{VII}$$

where $\Delta P = P - \rho h$.

The maximum speed $U_{f\,max}$ that can pour the fluid over a length L with a constant pouring speed is determined as follows $$U_{f\,max} = \frac{X}{L \cdot \epsilon} \qquad \text{VIII}$$

The final pressure of the fluid when it is poured at a constant speed $U_f$(cm/sec) over a length of L (cm) that is the pressure $P_n$ at the pouring port when the fluid overflows is expressed by $$P_n = \frac{(Fo + \lambda U_f L)}{\sqrt{1 - \frac{U_f}{U_{f\,max}}}} + \rho h \qquad \text{IX}$$

We have calculated the pressure P by determining $Fo_1$, $Fo_2$, $\lambda$, $\Delta Fo$ and coefficients from the equations described above. Further, we have obtained experimental values by pouring the fluid in an actual mould packed with an aggregate. The results of these calculations and experiments are shown in the following table 14 and the graphs shown in FIGS. 18a–18f.

In FIGS. 18a through 18f solid lines show experimental values and dotted lines the calculated values. Test No. 1 is shown by FIG. 18a which shows that the density of the coarse aggregate in the actual mould was slightly larger than that of the measuring device. Test No. 2 is shown by FIG. 18b which shows that the density of the coarse aggregate in the actual mould was also larger than that of the measuring device. The fact that the curves bend upwardly shows that both the actual mould and the measuring device had a tendency of clogging. Test No. 4 shown by FIG. 8c is similar to Test No. 1, and the Test No. 4 is an intermediate of Test Nos. 1 and 2. As shown by FIGS. 18d, 18e and 18f, in Test Nos. 5, 6 and 8 the conditions of packing of the coarse aggregate were substantially the same for the actual mould and the measuring device. The same is true for the Test No. 10. In the Test Nos. 6 and 9, the expected density made by the measuring device was higher than that of the actual mould. Although, there is a case wherein the condition in the actual mould can not accurately be expected by the result obtained by the measuring device the percentage of accurate expectation is about 33%. In certain cases the expected value (calculated value) is higher or lower than the actual value. However, since the results are distributed in substantially the same relationship so that the method of measurement and calculation are useful in practice. Even when the expected value deviates somewhat from the actual value this can be corrected as will be described later.

When pouring the plastic fluid into a mould packed with an aggregate, vibration has a large effect. Thus, a vibration having a frequency of from 5,000 to 40,000 $H_z$, more particularly from 10,000 to 20,000 $H_z$ has a tendency of decreasing the flow pressure P. However, vibrations having an extremely high frequency tends to increase the flow pressure. Where the pressure in the mould is reduced, the pouring pressure can be reduced.

Thus, according to the present invention, it is possible to correctly pour the plastic fluid into a mould by using the measured values of Fo, $\lambda$ and $\Delta$Fo. However, it is rare that the resistance element of the measuring device utilized to quantitatively determine the relative relationship between the factors relating to the flow passage and the fluid is quite the same as the resistance element in the actual mould. For example, even when the aggregates having the same grain size distribution and composition are used in the measuring device and the actual mould, the structures of the packed aggregates are not the same. Thus, there is a chance of forming a narrow passage or void in either one of the measuring device Table 14

| sample No. | | 1 | 2 | 3 | 4 | 5 | 6 | 7 | 8 | 9 | 10 |
|---|---|---|---|---|---|---|---|---|---|---|---|
| L type | $Fo_1$ (g/cm$^3$) | 1.66 | 3.47 | 3.36 | 4.11 | 1.85 | 0.79 | 2.84 | 2.35 | 2.22 | 0.22 |
| | $Fo_2$ (g/cm$^3$) | 1.83 | 4.17 | 4.01 | 5.13 | 1.98 | 1.16 | 3.07 | 2.44 | 2.42 | 0.27 |
| | $\lambda_1$ (g·sec/cm$^4$) | 2.38 | 9.26 | 8.88 | 13.20 | 2.85 | 4.76 | 8.60 | 0.70 | 1.20 | 1.08 |
| | $\Delta Fo$ (g/cm$^4$) | 0.0016 | 0.0114 | 0.0101 | 0.0231 | 0.0013 | 0.0032 | 0.0028 | 0.0016 | 0.0026 | 0.007 |
| coefficient | $C_0$ | 0.98 | 0.77 | 0.78 | 0.72 | 0.96 | 1.00 | 0.83 | 0.89 | 0.90 | 1 |
| | $C_1$ | 1 | 1 | 1 | 1 | 1 | 1 | 1.6 | 1.6 | 1.6 | |
| | $C_2$ | 1.9 | 1.9 | 1.9 | 1.9 | 1.9 | 1.9 | 1.9 | 1.9 | 1.9 | 1.9 |
| element | Fo (g/cm$^3$) | 1.63 | 2.67 | 2.62 | 2.96 | 1.78 | 0.79 | 2.36 | 3.35 | 3.27 | 0.35 |
| | $\lambda$ (g·sec/cm$^4$) | 2.33 | 7.13 | 6.93 | 9.50 | 2.74 | 4.76 | 7.14 | 1.00 | 1.73 | 1.73 |
| | X (cm$^2$/sec) | 48.0 | 20.3 | 21.4 | 14.7 | 53.8 | 33.6 | 39.4 | 36.5 | 31.1 | 56.8 |
| specific gravity | $\rho$ (g/cm$^3$) | 2.155 | 2.161 | 21.69 | 2.162 | 2.151 | 2.159 | 2.157 | 2.136 | 2.130 | 2.206 |
| speed | $U_f$ (cm/sec) | 0.240 | 0.217 | 0.232 | 0.221 | 0.228 | 0.185 | 0.326 | 0.182 | 0.188 | 0.178 |
| void factor | $\epsilon$ | 0.435 | 0.450 | 0.450 | 0.450 | 0.450 | 0.457 | 0.448 | 0.457 | 0.455 | 0.450 |
| pressure | calculated (g/cm$^2$) | 582 | 2701 | 5424 | ∞ | 611 | ∞ | 1843 | 4749 | 28 | 399 |
| | experimental (g/cm$^2$) | 26 | ∞ | 1402 | 1654 | 664 | 925 | 1791 | 2562 | 1990 | 473 | and the actual mould. This is especially remarkable where crushed stone is used as the coarse aggregate. Of course, the expectation is made by properly correcting the values measured by the measuring device but as has been pointed out hereinabove, such expected value is not always accurate. Variations in the factors are caused not only by the flow passage and the plastic fluid but also by the elapse of time. Accordingly, in order to have a correct pouring, such variables should also be considered. For this reason, in accordance with this invention in order to eliminate the effect of these variables, the pressure is controlled by controlling the pouring speed.

The relationship between the speed ($U_f$ in cm/sec) and the pressure (P in g/cm$^2$) is shown by a graph shown in FIG. 19. This graph shows that there is a residual pressure even when the speed is reduced to zero, the value of the residual speed corresponding to the product of the length L (cm) of the packed aggregate and Fo (g/cm$^3$). There is a limit for the pouring speed $U_f$. Beyond this limit the pressure become, infinity, thus resulting in the clogging. Further, decrease in the speed has a large influence upon the pouring pressure as shown by equations V to IX. For this reason, in accordance with this invention the pressure is controlled by the pouring speed by utilizing these facts. In the case of the constant quantity pouring (constant speed pouring), as the pouring distance varies, the pressure rises exponentially instead of linearly the curve showing appropriate pressure at respective points. Thus, the indication of the pouring pressure guage provided for the mould shows the difference from the appropriate pouring pressure.

Figure 20:
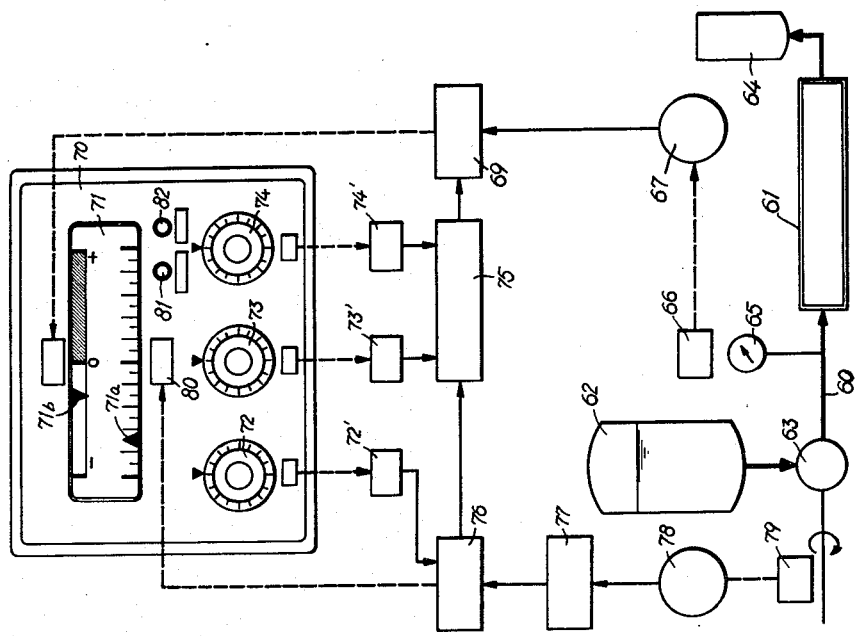
FIG. 20 is a block diagram showing one example of the pressure controlling system.

FIG. 20 shows a pressure controlling system designed by taking into consideration above described relationship. More particularly, a pouring tank 62 is connected to a mould 61 via a pump 63, the pouring pressure created by the pump 63 being indicated by a pressure gauge 65. For the mould 61 is generally used the prepacked process or underwater prepacked process. If desired, an overflow tank 64 may be connected to the mould 61 to confirm the completion of the pouring operation. A pressure detector 66 is provided for the pressure gauge for sending the detected pressure to a transducer 67 which sends an electric output to a comparator 69. A control panel 70 is provided including first to third setters 72, 73 and 74, a display member 71, a start button 81 and a stop button 82. The first setter 72 is used to set the number of revolutions of the pump 63 which is determined by the maximum pouring distance in the mould. The second setter 73 is used to set the pressure based upon the factors Fo, λ and ΔFo determined as above described, whereas the third setter 74 is used to set the coefficients described above. The first to third setters 72, 73 and 74 are connected with display members 72', 73' and 74', respectively. The first display member 72' is connected to a speed comparator 76 which is connected to a speed detector 79 of the pump 63 via a transducer 78 and a display member 77. Thus the comparator 76 compares the speed of the pump 63 at the end of the pouring with the set value of the pour distance and sends its output to the comparator 69 via a computer 75. The result of comparison made by the speed comparator 76 is also sent to the driving member 80 of the display member 71 for driving the pointer 71a thereof. The computer 75 operates either one of the following quations X, XI and XII $$P_n = P \cdot \sqrt{\frac{B-1}{B-\frac{N}{No}}} \cdot \frac{N}{No} + \rho h \qquad \text{X}$$

$$\text{where } B = \frac{C}{\sqrt{Fo \cdot U_f \epsilon L}}$$

The value of P is calculated by the equation described above.

$$P = A \left(\frac{N}{No}\right)^B \qquad \text{XI}$$

The solution of this equation is expressed by an approximate value of a secondary curve $$P = A \frac{N}{No} + B \qquad \text{XII}$$

The solution of this equation is expressed by an approximate value of a straight line.

Although either one of the equations X, XI and XII may be used, equation X is preferred where accuracy and safeness are important, but equation XI or XII may be used although accuracy is not so high.

The outputs of the second and third display members 73' and 74' are coupled with the computer 75 for obtaining an optimum pressure for respective settings in corporation with the signal from the speed comparator 76. The optimum pressure thus obtained is sent to the comparator 69 to be compared with the pouring pressure. The output thereof is used to drive the upper pointer 71b of the display member 71. Thus, pointer 71b shows the difference between the optimum pressure at respective points and the pouring pressure in the mould. On the other hand, the pointer 71a shows the pouring condition at respective points. Accordingly, accurate pourings can be assumed by modifying the pouring condition so that the actual condition will not largely deviate from the optimum condition. Thus, where the actual pouring pressure is larger than the optimum pressure, the speed of the pump 63 is reduced to reduce the actual pouring pressure to the optimum pressure.

As above described, according to the present invention, an optimum pouring pressure is predetermined and used as a reference and the actual pouring pressure is controlled in accordance with the pouring speed within a safe range. Alternatively a reference pressure diagram may be prepared by using the values calculated by the above described equations for the purpose of carrying out the actual pouring operation.

Figure 21:
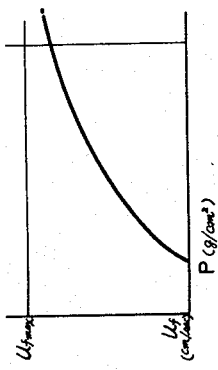
FIG. 21 shows a pressure diagram to be used as the reference.

FIG. 21 illustrates one example of such diagram in which the ordinate represents the pressure P and the abscissa the pouring distance L of the total pouring quantity ΣQ. From this curve it is possible to determine the pressure at any point until a predetermined pouring pressure Po is reached. Also it is possible to set a maximum pressure $P_{max}$. Since the pressure corresponds to the speed of the pump for respective $U_f$. Accordingly, a desired moulding can be attained if the pouring operation is performed according to the curve without any appreciable departure.

Figure 22:
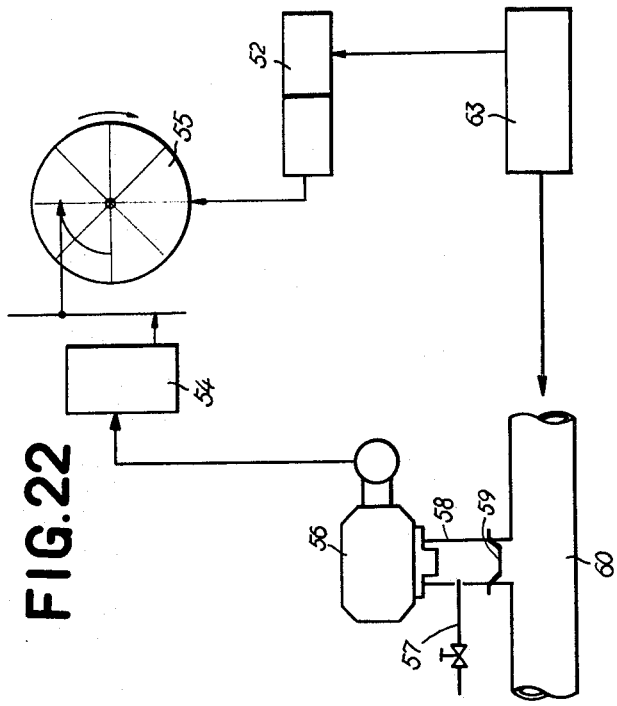
FIG. 22 is a block diagram showing another example of the pressure controlling system embodying the invention.
Figure 23:
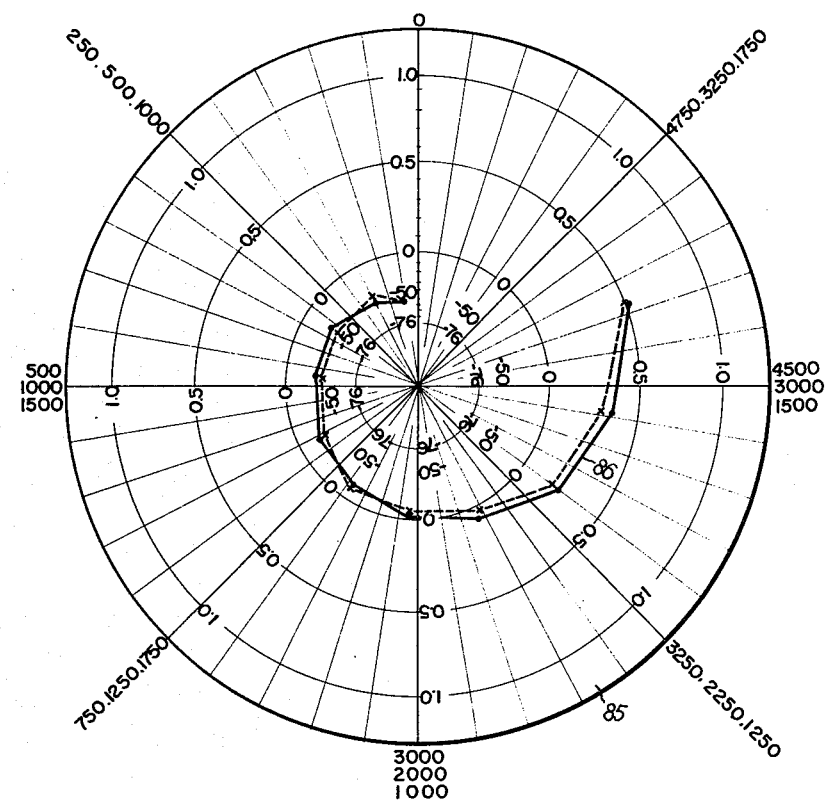
FIG. 23 is a plan view showing the recording chart utilized in the embodiment shown in FIG. 22.

FIG. 22 shows another example of the pressure control system. In this example, a pressure transmitter 56 is connected to a pouring conduit 60 connected to the pump 63, via tube 58 including diaphragms 59. Isolation liquid is supplied to the space between the diaphragms 59 via a pipe 57. The pressure transmitter 56 produces an electrical signal supplied to a pen operating device 54 of a recorder. The pen operating device 54 operates a pen, not shown, to depict a diagram on a recording paper 85 as shown in FIG. 23 and mounted on a rotary disc 55 which is driven by the pump 63 through a speed reducing gear train 52. The recording paper 85 is printed with a predetermined pressure 86 and a safety zone so that the operator controls the pouring condition by watching the recording paper and the actual pressure is recorded on the recording paper. The control system shown in FIG. 22 is more compact than that shown in FIG. 20 and can produce records of the pouring pressure.

Figure 24:
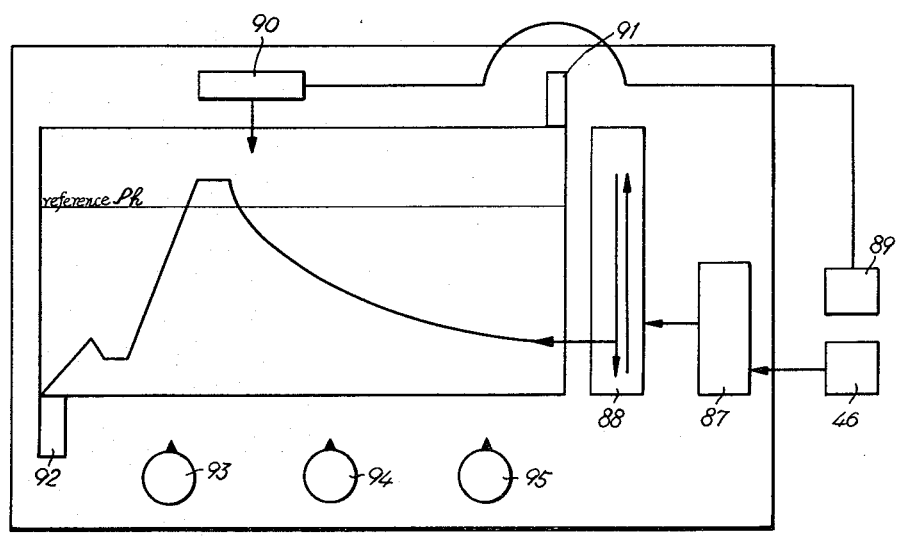
FIG. 24 is a block diagram utilized in the recording device shown in FIG. 17 for automatic display and recording.

FIG. 24 is a diagrammatic representation of a recording device utilized to record the result of measurement made by the measuring device shown in FIG. 17, for example. The electric signal generated by the differential transmitter 46 shown in FIG. 17 is applied to a pointer driver 88 via a pressure transducer 87. The fact that the poured plastic fluid has reached a definite level, for example 60 cm above the packed aggregate layer shown in FIGS. 13 through 17 is detected by a level sensor 89. The signal generated by the level detector 89 is used to operate a printing mechanism 90 when switch 95 is operated. A recording paper feed mechanism 91 is operated by a switch 94. There are also provided a switch 93 for operating the differential transmitter 46 and a cutter 92 which is used to cut the recording paper upon completion of the recording operation.

According to the present invention, since the optimum pouring pressure is established it is possible to determine the actual pouring operation and correctly execute the same. More particularly, in the moulding operation of concrete, the strength and the configuration of the product, and process steps (time) are given. Among these factors, the strength of the product is determined by the water to cement ratio and can be assured by Fo, λ, ΔFo which are obtained by an optimum composition. Factors Fo, λ and ΔFo are used to determine the actual pouring speed as well as the pouring pressure by considering the process time and safety factor. When the pouring pressure is determined, the rigidity of the mould frame can be determined from the pouring pressure and the pressure applied during the cure period. Thus, it will be clear that according to this invention it is possible to obtain products having uniform and high quality because in the past the pouring pressure or speed has be determined by the feeling and experience of the operator without relying upon any definite reference or index.

In the preparation of a concrete mortar, Fo, λ and ΔFo are suitably modified by taking into consideration such factors as the water content of the sand, the order of incorporating respective ingredients, and the compounding time should the result of measurement departs from the expected values, the ratio C/S may be varied without changing the ratio W/C. Alternatively, the operating condition may be corrected by varying the pouring speed where the pouring pressure departs greatly from the optimum pouring pressure or by incorporating a suitable dispersion agent.

The following description illustrates some examples of the present invention.

EXAMPLE 1

Sand and cement were mixed together at a ratio of 1:1, and 1.3% of a dispersion agent based on the weight of the cement and 48% of water based on the weight of the cement were added to prepare a cement mortar. When measured by the measuring device utilizing a reference aggregate comprising glass beads having a diameter of 2.5 mm and packed over a length of 10 cm the cement mortar thus prepared showed a static head difference of 5 cm immediately after compounding, 5.5 cm after 30 minutes under room temperature and 6.3 cm after 60 minutes. The flow value of the mortar was determined by using a conventional P funnel and found that the flow value was 23 seconds immediately after compounding, 44 seconds after 30 minutes, and 98 seconds after 60 minutes. It has been considered that the concrete mortar having such high flow values is difficult to pour with conventional prepacked technique and hence deemed as an improper mortar. Generally, a mortar having a flow value longer than 20 seconds is difficult to pour and that having a flow value longer than 30 seconds is impossible to pour.

The cement mortar described above was poured under a pouring pressure of 0.7 Kg/cm$^2$ into a mould packed with No. 4 crushed stone. The mortar was uniformly poured into the mould and a cylinder was cut out of the moulded product to inspect the poured condition. The result was satisfactory.

EXAMPLE 2

Sand and water were mixed together at a ratio of 1:1 and 0.5% based on the weight of cement of a dispersion agent and 48%, based on the weight of the cement of water, were added. The flow value of the compounded cement mortar was measured by using a conventional P funnel. The measured flow value was 18 seconds which is sufficient to pour. The static head difference of this mortar measured by the measuring device described above was 220 mm immediately after compounding, 240 mm after 30 minutes and 295 mm after 60 minutes showing that the mortar is difficult to pour.

When this mortar was carefully poured under the same conditions as in Example 1, the pouring at various portions of the mould was not perfect showing that the mortar is not suitable for practical use.

EXAMPLE 3

Cement, 1.3% of a dispersion agent and water were compounded to obtain a cement paste having a water to cement ratio of 40%.

The static head difference measured by the measuring device described above and the flow value measured by the conventional P funnel are shown in the following Table 15.

Table 15

| | flow value | static head difference |
|---|---|---|
| immediately after compounding | 55 sec. | 30 mm |
| after 30 min. | 65 sec. | 40 mm |
| after 60 min. | ∞ | 48 mm |

Although a cement paste having a flow value shown in this table has been considered difficult to pour, it can be poured by using the static head difference determined in accordance with this invention. For example, we have succeeded to uniformly pour into a mould prepacked with No. 4 crushed stone under reduced pressure. The product thus prepared had a compression strength of 5 Kg/cm$^2$.

EXAMPLE 4

Cement and sand were admitted at a ratio of 1:1, and 1.3%, based on the weight of the cement, of a dispersion agent and water were incorporated to obtain a cement mortar having a water to cement ratio of 45%. The flow value of this mortar determined by the P funnel was 20 seconds. The static head difference of this mortar determined by a measuring device as shown in FIG. 10 and packed with glass beads having a diameter of 20 mm over a length of 20 mm was 18 cm. After closing the discharge port with a steel sheet lid, the mortar was poured into the pouring port to a height of 100 cm in terms of the static head difference the lid was removed permitting the mortar to overflow. The falling speed of the level between the static head difference of 60 cm and the static head difference of 40 cm was 2 cm/sec. on an average, and the end static head difference was 18.5 cm which is to be compared with the initial value of 18 cm. This means that a solid component, that is sand did not deposited in the void of the coarse aggregate.

In the same manner, cement and sand at a ratio of 1:1.3, 1.3% based on the weight of the cement of a dispersion agent and water were mixed together to prepare a cement mortar having a water to cement ratio of 52%. The flow value of this mortar measured by the P funnel was 23 seconds. The static head difference of this mortar measured by the measuring device shown in FIG. 8 and packed with glass beads having a diameter of 20 mm over a length of 20 cm was 20 cm. After closing the discharge port with a steel sheet lid the mortar was poured into the pouring port to a hegiht of 100 cm in terms of the static head difference. Thereafter, the lid was removed to permit the mortar to overflow and the falling speed of the mortar level in the leg including the pouring port was measured. The mean falling speed of the level from the static head difference of 60 cm to the static head difference of 40 cm was 2.3 cm/sec. and the end static head difference was 30 cm showing 10 cm increase in the static head difference. Such increase in the static head difference shows deposition of the solid particles as sand in the void of the coarse aggregate.

The two mortars described above were respectively poured into moulds each having a width of 1000 mm, a length of 2000 mm and a height of 120 mm and evacuated to a pressure of 24 mm Hg. The pressure difference necessary to pour was 0.8 Kg/cm$^2$ and 1.5 Kg/cm$^2$, respectively. In the later mortar a substantial amount of the water segregated at the time of pouring was observed through a transparent window of the mould. This may be attributed to the deposition of the sand.

EXAMPLE 5

Sand and cement at a ratio of 1:1.3, 1.3% based on the weight of the cement of a dispersion agent, and water were mixed together to obtain a cement mortar having a water to cement ratio of 52%. The flow value of this cement measured by the P funnel was 23 seconds. The head difference of this mortar was measured by the measuring devices as shown in FIG. 10 respectively packed with No. 4 crushed stone over a length of 10 cm, 15 cm and 20 cm. The static head difference was 12 cm for the packed length of 10 cm, 15 cm for the packed length of 15 cm and 20 cm for the packed length of 20 cm. The variation of the shear stress yielding value of the mortar caused by the difference in the static head difference due to different packed lengths of the coarse aggregate (No. 4 crushed stone) was investigated by using a flat mould having a length of 4 m and packed with the aggregate of the same type. The shear stress yielding value was 245 g/cm$^2$ for the packed lengths of 10 cm and 15 cm, and 405 g/cm$^2$ for the packed lengths of 15 cm and 20 cm showing that the initial shear stress yielding value will increase with the packed length.

Accordingly, when pouring the mortar into an actual mould having a length of 4 m, the pouring conditions were determined on the assumption that the initial shear stress yielding value would be 700 g/cm$^2$, and the mortar was poured with an initial pouring speed of 1 cm/sec. The result was satisfactory.

Figure 25:
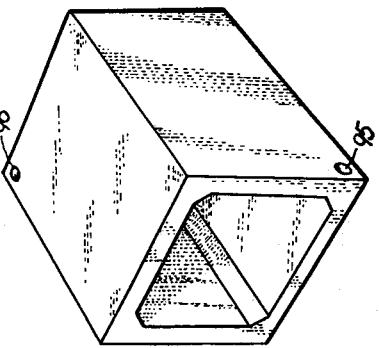
FIG. 25 is a perspective view showing the relative arrangement of a pouring port and an overflow port when moulding a box calvert.

The mortar was used to mould a box calvert as shown in FIG. 25 and having a width, length and height of 1500 mm each, and a wall thickness of 150 mm. The box calvert was required to have a compression strength of 400 Kg/cm$^2$, and the preferred production speed was 15 min. The sand utilized to prepare the box calvert had a specific gravity of 2.5 g, a fineness modulus of 1.96, and a percentage of water absorption of 2.6%. The box calvert shown in FIG. 25 had a pouring port 95, 200 mm above the bottom and a pouring port 96 at a diagonally opposite position with respect to the pouring port. The void factor E of the packed aggregate was 0.45. A 6000 Hz vibrator was used during the pouring operation until 30 second before the level of the poured mortar had reached the overflow opening 96. The mould was constructed to withstand a pressure of 520 mm Hg.

With the data described above, the pouring conditions were calculated as follows according to the equations described above: pouring distance L $_{max}$ = 1850 cm (c = 9.6), height h = 150 cm, $\rho$ = 2.165, Fo = 0.57, $\Delta$Fo = 0.0044 ($\sqrt{\Delta Fo}$ = 0.066) $\lambda$ = 3.21, U$_f$ = 0.5, $\epsilon$ = 0.45, actual maximum pouring distant L $_{max}$ = 646.46 cm. Under these conditions the total pouring pressure was calculated as $\Delta$P = 1217 g/cm$^2$.

Furthermore, the mortar composition was determined as follows from the conditions described above: the ratio W/C = 38%, the ratio C/S = 1:1, cement = 180 kg, sand = 180 Kg, water = 68.4 Kg, dispersion agent = 1.0%. The weight per unit volume of the mortar was 2.165 Kg/l which is equal to the value of $\rho$ just described. The mortar prepared by compounding these ingredients had a fluidity of 0.65, $\Delta$Fo = 0.0047 g/cm$^3$.cm, and $\lambda$ of 3.75 these values satisfying the requirements described above.

The mortar was poured into the practical mould described above at a pouring speed of U$_f$ = 0.5 cm/sec. The pouring step was controlled such that the actual pouring pressure will not exceed the calculated pouring pressure for the pouring time T. The time required for the pouring was 13 minutes and the number of revolution of the pump was 160 R.P.M. on an average. When poured at a rate of 80 l per minute, the mortar was poured uniformly without void throughout the mould.

EXAMPLE 7

Figure 26:
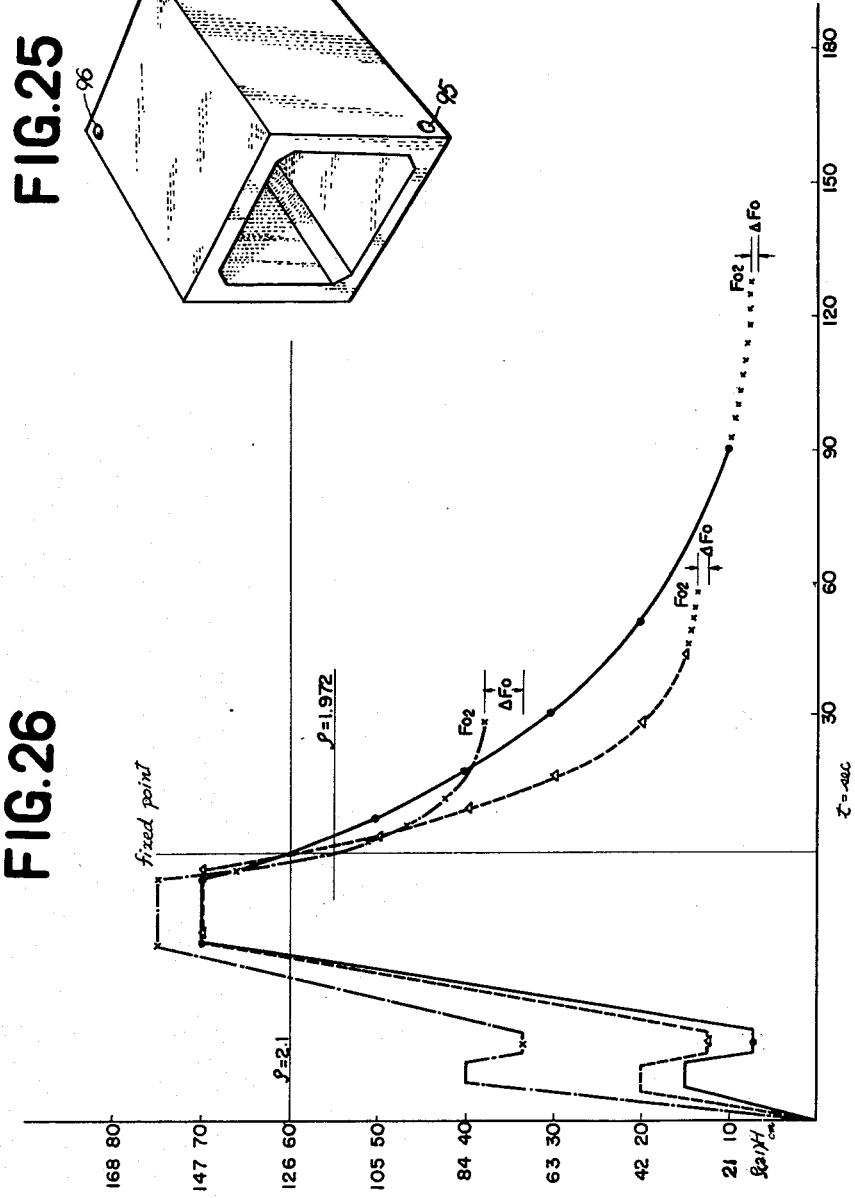
FIG. 26 is a graph showing some results of measurement obtained by the recording device shown in FIG. 24.

The fluidity of various mortars prepared by the control system shown in FIG. 24 was measured and the result are shown by the graph of FIG. 26. The No. 1-A sample shown by solid lines had a C/S ratio of 1:1, the fineness modulus of the sand of 1.89 and a W/C ratio of 38%. The No. 6-A sample shown by dotted lines had a C/S ratio of 1:1, the fineness modulus of the sand of 1.66 and a W/C ratio of 37%. The No. 16-A sample shown by dot and dash lines had a C/S ratio of 1:1, the fineness modulus of the sand of 1.54 and a W/C ratio of 36%.

The fluidity of three types of the mortar was measured and the results are shown in the following Table 16.

Table 16

| sample No. | | 1-A | 6-A | 16-A |
|---|---|---|---|---|
| $Fo_1$ | $g/cm^3$ | 0.74 | 1.31 | 3.50 |
| | cm | 7.0 | 12.5 | 35.5 |
| $Fo_2$ | $g/cm^2$ | 0.77 | 1.42 | 3.94 |
| | cm | 7.3 | 13.5 | 40.0 |
| $\Delta Fo$ | $g/cm^4$ | 0.00048 | 0.002 | 0.0011 |
| | cm | 0.3 | 1.0 | 4.5 |
| $\lambda$ (mean value) | | 3.85 | 1.58 | 0.83 |
| additive (%) | | 1 | 1 | 0 |
| water content of sand (%) | | 6.8 | 7.0 | 9.9 |

Based on the differential pressure at the time of passing the definite points, these 3 mortars were found to have $\rho$ of 2.1 for sample 1-A, 2.1 for sample 6-A and 1.97 for sample 16-A. These three mortars were poured into a closed mould packed with a coarse aggregate at a void factor $\epsilon = 0.45$ in an interval of 6 minutes each to prepare building blocks each having a dimension of 1 m $\times$ 2 m $\times$ 15 cm. The mould was constructed to withstand a pressure of $\pm$ 1.7 Kg/cm$^2$. The end pouring pressure $\Delta P$ was calculated as 0.58 Kg/cm$^2$ for sample 1-A, 0.68 Kg/cm$^2$ for sample 16-A and 1.2 Kg/cm$^2$ for sample 16-A.

Each of the end pouring pressures $\Delta P$ is included in the range of the mould strength showing that the mould can be used practically. Accordingly, the three mortars could successfully be poured into the mould under the end pouring pressure and pouring time conditions. The compression strength of the concrete plate thus moulded and 4 weeks after casting was 430 Kg/cm$^2$ for sample 1-A, 450 Kg/cm$^2$ for sample 6-A and 460 Kg/cm$^2$, showing the quality of the product is excellent.

As above described, according to the present invention, the characteristics of a plastic fluid containing solid ingredients such as cement mortar, cement paste and kneaded refractory compounds are analyzed and measured by passing the plastic fluid through a resistive passage that is a passage packed with an aggregate, and actual poured conditions predetermined by using the result of analysis and measurement. Consequently, it becomes possible to construct prepacked concrete structures and refractories of high quality at high efficiency. It is also possible to simultaneously and continuously measure various characteristics of the plastic fluid and to control the pouring conditions automatically. According to the present invention, it is possible to satisfactorily mould such mortar or paste which has been considered to be not suitable to cast, by predetermining optimum pouring conditions.

What is claimed is:

1. A method for measuring the fluidity of a plastic fluid showing the characteristics of a Bingham Fluid System which requires an initial shear stress yielding pressure to cause it to flow, comprising the steps of providing an element defining a flow passage through which said fluid is passed which manifests a resistance to the flow of said plastic fluid, passing said plastic fluid through said flow passage, and measuring the pressure necessary to cause said plastic fluid to flow through said flow passage for determining the relative flow coefficients of said plastic fluid with respect to said flow passage, said coefficients being the relative initial shear stress yielding value, the relative closure coefficient and the relative flow viscosity coefficient.

2. The method according to claim 1, wherein said flow passage is packed with a resistive element.

3. A method of measuring the pouring characteristic of a plastic fluid containing a solid component comprising the steps of preparing a U shaped passage, packing an aggregate in said passage for a predetermined length, pouring said plastic fluid into said passage, and measuring the static head difference between the plastic fluid levels on both sides of the packed aggregate, said static head difference being caused by said packed aggregate.

4. The method according to claim 3 which further comprises the steps of, after measuring said static head difference, pouring a predetermined quantity of said plastic fluid into said passage, measuring again the pressure difference, and determining the pressure created by the deposition of said solid component on said aggregate in accordance with the difference in said successively measured static head differences.

5. The method according to claim 4, wherein the aggregate is glass beads and the results of the measurements are corrected by the predetermined correction coefficient.

6. A method of measuring the pouring characteristic of a plastic fluid containing a solid component comprising the steps of preparing a U shaped tube, packing an aggregate in said tube for a predetermined length, pouring said plastic fluid into said tube through one end thereof with the other end closed, opening said other end thereby permitting said plastic fluid to flow through said aggregate, measuring the flow quantity and flow time of said plastic fluid thereby determining the flow rate, and measuring the static head difference between the plastic fluid levels on both sides of the packed aggregate, and determining the shear stress yielding value of said plastic fluid from said static head difference.

7. A method of preparing a plastic fluid adapted to be poured into a mould prepacked with an aggregate, said method comprising the steps of providing an element defining a flow passage, introducing the aggregate into the flow passage, said aggregate manifesting a resistance to the flow of the plastic fluid thereby simulating said mould, passing said plastic fluid through said flow passage, measuring the pressure necessary to initiate the flow of said plastic fluid through said flow passage, quantitatively determining the relative shear stress yielding value of said plastic fluid with respect to said flow passage, determining again the relative shear stress yielding value after passing a predetermined amount of said plastic fluid through said flow passage, quantitatively determining the relative closure coefficient of said plastic fluid with respect to said flow passage from the difference between said first and second mentioned relative shear stress yielding values, causing said plastic fluid to flow through said flow passage under a varying flow speed, measuring the relationship between the speed and the pressure said plastic fluid, determining the relative flow viscosity coefficient of said plastic fluid with respect to said flow passage, and determining the fluidity of said plastic fluid in accordance with said relative closure coefficient and said relative flow viscosity coefficient determined as above described.

8. A method of preparing a prepacked concrete article comprising the steps of preparing a measuring device including a curved tube packed with an aggregate over a predetermined length, pouring a plastic fluid containing a hydraulic setting substance into said tube, measuring the static head difference between the plastic fluid levels on both sides of said aggregate, determining the shear stress yielding value of said plastic fluid from said static head difference, determining the pouring condition of said plastic fluid in accordance with said shear stress yielding value, and pouring said plastic fluid under said pouring condition into a mould prepacked with an aggregate.

9. The method according to claim 8 in which a plurality of said measuring devices packed with said aggregate for different lengths are used, the static head differences measured by respective measuring devices are used to determine the state of variation of the shear stress yielding value of said plastic fluid due to the difference in the length of the packed zone of said aggregate, and the pouring condition of said plastic fluid determined in accordance with the shear strength yielding value and the state of variation thereof.

10. A measuring device for measuring the fluidity of a plastic fluid having the characteristics of a Bingham Fluid System which requires an initial shear stress yielding pressure to cause it to flow, comprising a tube having a pouring port at one end and a discharge port at the other end, a resistance element packed in said tube at an intermediate portion thereof for a predetermined length for affording a resistance to the flow of said plastic fluid, means for causing the plastic fluid to flow through said resistance element, and means for measuring the fluid pressure of said plastic fluid.

11. The measuring device according to claim 10 wherein said tube takes the form of a straight tube, one end thereof being immersed in said plastic fluid.

12. The measuring device according to claim 10 wherein said plastic fluid contains a solid component, and said tube comprises a pair of spaced vertical legs and a horizontal leg interconnecting the lower portions of said vertical legs, one of said vertical leg including a pouring port for said plastic fluid and the other leg including a discharge port.

13. The measuring device according to claim 12 wherein the lower ends of said vertical legs terminate beneath said horizontal leg so as to form chambers for accumulating the solid component segregated from said plastic fluid.

14. The measuring device according to claim 10 which further comprises means for recording the pressure of said plastic fluid in said tube and means for recording the fact that said fluid has passed through a definite point along said tube.

15. A control system for pouring a plastic fluid into a mould packed with an aggregate comprising a pump for pouring said plastic fluid into said mould, means for detecting the pressure of the plastic fluid poured into said mould, means for detecting the speed of said pump, a first comparator for comparing the detected speed with a predetermined reference speed, means for setting a predetermined pressure condition of said plastic fluid, means for setting the physical characteristics of said plastic fluid, a computer for calculating an optimum pouring pressure of said plastic fluid in accordance with the output from said first comparator, said predetermined pressure condition, and said physical characteristics, a second comparator for comparing the output from said computer and the output of said pressure detecting means, first display means for displaying the output from said first comparator, and a second display means for displaying the output from said second comparator.

16. A method of pouring a plastic fluid into a mould containing a resistive element which resists the flow of said plastic fluid, said plastic fluid showing the characteristics of a Bingham Fluid System which requires an initial shear stress yielding pressure to cause it to flow, comprising the steps of providing a model passage simulating the condition of said mould, passing plastic fluid through said passage, measuring the fluid pressure for determining the relative flow coefficients of said plastic fluid with respect to said mould, said coefficients being the relative initial shear stress yielding value, the relative closure coefficient and the relative viscosity coefficient, planning pouring conditions in accordance with the following equation:

$$P_{(t)} = K \sqrt{\frac{X}{X - \int_0^t U_f^2 \cdot dt}} (F_O + \lambda U_f) \int_0^t U_f \cdot dt + \rho h$$

$$X = \frac{C}{\sqrt{\Delta F_O}}$$

where
$P_{(t)}$ = flow pressure, g/cm$^2$
$t$ = flow time, sec
$F_O$ = relative shear stress yielding value, g/cm$^3$
$U_f$ = flow speed, cm/sec
$\lambda$ = relative flow viscosity coefficient, g.sec/cm$^4$
$h$ = height of mould, cm
$C$ = supplemental value determined with respect to each fluid and mould by pre-experiments, $\sqrt{g}$/sec
$K$ = supplemental value determined with respect to each fluid and mould by pre-experiments (no dimensions)
$\rho$ = weight of the unit of the plastic fluid, g/cm$^3$
$\Delta F_O$ = relative closure coefficient, g/cm$^4$
said conditions being the flow speed, the flow pressure, and the flow time, and controlling the flow speed, the flow pressure, and the flow time of said plastic fluid poured into said mould.

17. A measuring device for measuring the fluidity of a plastic fluid comprising a U-shaped tube having a pouring port at one end and a discharge port at the other end, a resistance element of predetermined length packed in the leg of said U-shaped tube having the discharge port, for affording a resistance to the flow of said plastic fluid, means for causing said plastic fluid to flow through said resistance element and means for measuring the fluid pressure of said plastic fluid.

18. The measuring device according to claim 17 wherein said one leg containing the resistance element is provided with a removable lid, and when said lid is removed, the plastic fluid in said tube moves under the atmospheric pressure.

19. The measuring device according to claim 17 wherein said measuring device is provided with a pressure detector for detecting the pressure of said plastic fluid at the bottom of the measuring device.

20. A measuring device for measuring the fluidity of a plastic fluid, comprising an L-shaped tube having a pouring port at one end and a discharge port at the other end, one leg of said L-shaped tube being immersed in said plastic fluid, a resistance element packed in said tube at an intermediate position thereof for a predetermined length for affording a resistance to the flow of said plastic fluid, means for causing said plastic fluid to flow through said resistance elements, and means for measuring the fluid pressure of said plastic fluid.

21. A measuring device for measuring the fluidity of a plastic fluid containing a solid component, including a tube comprising a pair of spaced-apart vertical legs and a horizontal leg interconnecting the lower portions of said vertical legs, one of said vertical legs including a pouring port for said plastic fluid and the other leg including a discharge port, a resistance element of a predetermined length packed in said other leg for affording a resistance to the flow of said plastic fluid, means for causing said plastic fluid to flow through said resistance element, and means for measuring the fluid pressure of said plastic fluid.

22. A measuring device for measuring a fluidity of a plastic fluid containing a solid component, including a tube comprising a pair of spaced-apart vertical legs and a horizontal leg interconnecting the lower portions of said vertical legs, one of said vertical legs including a pouring port for said plastic fluid and the other leg including a discharge port, a resistance element of a predetermined length packed in said horizontal leg for effecting a resistance to the flow of said plastic fluid, means for causing said plastic fluid to flow through said resistance element, and means for measuring the fluid pressure of said plastic fluid.

23. A measuring device for measuring the fluidity of a plastic fluid containing a solid component, including a tube comprising a pair of spaced-apart vertical legs and a horizontal leg interconnecting the lower portions of said vertical legs, said horizontal leg having a relatively large volume for accumulating the solid component segregated from said plastic fluid, one of said vertical legs including a pouring port for said plastic fluid and the other leg including a discharge port, a resistance element packed in said tubes at an intermediate portion thereof for a predetermined length for affording a resistance to the flow of said plastic fluid, means for causing said plastic fluid to flow through said resistance element, and means for measuring the fluid pressure of said plastic fluid.

24. A measuring device for measuring the fluidity of a plastic fluid containing a solid component including a tube comprising a pair of spaced-apart vertical legs and a removable horizontal leg interconnecting the lower portion of said vertical legs, one of said vertical legs including a pouring port for said plastic fluid and the other leg including a discharge port, a resistance element packed in said tube at an intermediate position thereof for a predetermined length for affording a resistance to the flow of said plastic fluid, means for causing said plastic fluid to flow through said resistance element, and means for measuring the fluid pressure of said plastic fluid.

25. A measuring device for measuring the fluidity of a plastic fluid, comprising a tube having a pouring port at one end and a discharge port at the other end, a resistance element packed in said tube at an intermediate portion thereof for a predetermined length for affording a resistance to the flow of said plastic fluid, means for causing said plastic fluid to flow through said resistance element, and means for measuring the fluid pressure of said plastic fluid, wherein said plastic fluid comprises a cement mortar or paste or cement adapted to be poured into a mould packed with an aggregate or reinforcing bar, and said resistance element comprises particulate substance simulating the characteristic of said aggregate.

26. A method of measuring the fluidity of a plastic fluid comprising the steps of providing an element defining a flow passage which manifests a resistance to the flow of said plastic fluid, passing said plastic fluid through said flow passage, measuring the pressure necessary to cause said plastic fluid to flow through said flow passage, and quantitatively determining the relative shear stress yielding value of said plastic fluid with respect to said flow passage, said relative shear stress yielding value being represented by the equation:

$$F_o = (P/l)$$

where
$F_o$ = shear stress yielding value, g/cm$^3$
$P$ = pressure necessary to start the flow through the passage, g/cm$^2$
$l$ = length of the model passage, cm.

27. The method according to claim 26, wherein said fluid is caused to flow through the flow passage by gravity, and the pressure of the fluid when the flow speed has been reduced to zero is measured, thus quantitatively measuring said relative shear stress yielding values represented by the following equation:

$$F_o = (P_1/l)$$

where
$P_1$ = pressure of the fluid when the flow speed thereof has been reduced to zero (g/cm$^2$).

28. The method according to claim 26, which further comprises the steps of determining again the relative shear stress yielding value and quantitatively determining the relative closure coefficient of said plastic fluid with respect to said flow passage represented by the undermentioned equation from the difference between said first and second mentioned relative shear stress yielding values:

$$\triangleleft F_o = \frac{(F_{o2} - F_{o1}) A}{Q}$$

where
$\triangleleft F_o$ = relative closure coefficient (g/cm.cm),
$F_{o1}$ = first relative shear stress yielding value (g/cm$^3$),
$F_{o2}$ = second relative shear stress yielding value (g/cm$^3$),
$Q$ = quantity of the fluid passing through the flow passage during the second measurement for the relative shear stress yielding value (cm$^3$), and
$A$ = cross-sectional area of the flow passage (cm$^2$).

29. A method of measuring the fluidity of a plastic fluid comprizing the steps of providing an element defining a flow passage which manifests a resistance to the flow of said plastic fluid, passing said plastic fluid through said flow passage, measuring the pressure necessary to cause said plastic fluid to flow through said flow passage, and quantitatively determining the relative flow coefficients of said plastic fluid with respect to said flow passage, wherein said plastic fluid is caused to flow through said flow passage under varying flow speeds, the relationship between said flow speed and the fluid pressure of said plastic fluid at the inlet side of the flow passage is measured, and the relative flow viscosity coefficient of said plastic fluid with respect to said passage is measured and represented by the following equation:

$$\lambda = (P_u/U_f)$$

where $\lambda$ = relative flow viscosity coefficient, g.sec/cm$^3$.cm
$P_u$ = pressure of the fluid at each flow speed thereof per the unit length of the resistive element, g/cm$^3$
$U_f$ = flow speed of the fluid, cm/sec.

30. A measuring device for measuring the fluidity of a plastic fluid having the characteristics of a Bingham Fluid System which requires an initial shear stress yielding pressure to cause it to flow, comprising a tube having a pouring port at one end and a discharge port at the other end, a resistance element packed in said tube at an intermediate portion thereof for a predetermined length for affording a resistance to the flow of said plastic fluid, means for causing said plastic fluid to flow through said resistance element, and means for measuring the fluid pressure of said plastic fluid, wherein said measuring means is connected to the tank of a concrete mixer through a valve.

* * * * *

UNITED STATES PATENT AND TRADEMARK OFFICE
CERTIFICATE OF CORRECTION

PATENT NO. : 4,143,541
DATED : March 13, 1979
INVENTOR(S) : Yasuro ITO et al

It is certified that error appears in the above-identified patent and that said Letters Patent are hereby corrected as shown below:

IN THE HEADING:

Under Foreign Application Priority Data, delete the following:

"Jan. 27, 1976 [JP] Japan ................. 51-7132"

Signed and Sealed this

Thirteenth Day of May 1980

[SEAL]

Attest:

SIDNEY A. DIAMOND

Attesting Officer     Commissioner of Patents and Trademarks